(12) United States Patent
Ahmad

(10) Patent No.: US 12,370,333 B2
(45) Date of Patent: *Jul. 29, 2025

(54) PORTABLE MEDICAL VENTILATOR SYSTEM USING PORTABLE OXYGEN CONCENTRATORS

(71) Applicant: Ventec Life Systems, Inc., Bothell, WA (US)

(72) Inventor: Samir Saleh Ahmad, San Diego, CA (US)

(73) Assignee: Ventec Life Systems, Inc., Bothell, WA (US)

( * ) Notice: Subject to any disclaimer, the term of this patent is extended or adjusted under 35 U.S.C. 154(b) by 729 days.

This patent is subject to a terminal disclaimer.

(21) Appl. No.: 17/521,810

(22) Filed: Nov. 8, 2021

(65) Prior Publication Data

US 2022/0313932 A1 Oct. 6, 2022

Related U.S. Application Data

(63) Continuation of application No. 16/381,897, filed on Apr. 11, 2019, now Pat. No. 11,191,915.

(Continued)

(51) Int. Cl.
*A61M 16/00* (2006.01)
*A61M 16/04* (2006.01)
(Continued)

(52) U.S. Cl.
CPC ...... *A61M 16/022* (2017.08); *A61M 16/0003* (2014.02); *A61M 16/0066* (2013.01);
(Continued)

(58) Field of Classification Search
CPC ............ A61M 16/022; A61M 16/0003; A61M 16/0672; A61M 16/0883; A61M 16/101;
(Continued)

(56) References Cited

U.S. PATENT DOCUMENTS 3,191,596 A 6/1965 Bird
3,234,932 A 2/1966 Bird
(Continued)

FOREIGN PATENT DOCUMENTS

CN 87206076 U 4/1988
CN 2718262 Y 8/2005
(Continued)

OTHER PUBLICATIONS

US 8,012,240, 11/2008, Sprinkle (withdrawn).
(Continued)

*Primary Examiner* — Steven O Douglas
(74) *Attorney, Agent, or Firm* — Perkins Coie LLP

(57) ABSTRACT

A portable medical ventilator using pulse flow from an oxygen concentrator to gain higher oxygen concentration includes a positive pressure source to deliver pressurized air to the patient and a negative pressure source to trigger the oxygen concentrator. A patient circuit attached to a patient interface mask connects the ventilator to the patient. The ventilator includes a controller module that is configured to generate a signal to the negative pressure device to trigger the concentrator to initiate one or more pulses of oxygen from the oxygen concentrator. The oxygen pulses are delivered to the patient interface directly through multi-tube or a multi lumen patient circuit. The oxygen does not mix with air in the ventilator or in the patient circuit and bypasses the leaks in the patient circuit and/or patient interface.

20 Claims, 7 Drawing Sheets

Related U.S. Application Data

(60) Provisional application No. 62/670,856, filed on May 13, 2018.

(51) Int. Cl.
*A61M 16/06* (2006.01)
*A61M 16/08* (2006.01)
*A61M 16/10* (2006.01)
*A61M 16/12* (2006.01)

(52) U.S. Cl.
CPC ............ *A61M 16/04* (2013.01); *A61M 16/06* (2013.01); *A61M 16/0672* (2014.02); *A61M 16/0875* (2013.01); *A61M 16/0883* (2014.02); *A61M 16/101* (2014.02); *A61M 16/12* (2013.01); *A61M 2016/003* (2013.01); *A61M 2202/0208* (2013.01)

(58) Field of Classification Search
CPC .. A61M 16/0066; A61M 16/04; A61M 16/06; A61M 16/0875; A61M 16/12; A61M 2016/003; A61M 2202/0208
See application file for complete search history.

(56) References Cited

U.S. PATENT DOCUMENTS

| | | |
|---|---|---|
| 3,789,837 A | 2/1974 | Philips et al. |
| 3,806,102 A | 4/1974 | Valenta et al. |
| 3,875,626 A | 4/1975 | Tysk et al. |
| 3,993,059 A | 11/1976 | Sjostrand |
| 4,280,399 A | 7/1981 | Cunning |
| 4,331,455 A | 5/1982 | Sato |
| 4,357,936 A | 11/1982 | Ellestad et al. |
| 4,367,767 A | 1/1983 | Hurd |
| 4,386,945 A | 6/1983 | Gardner |
| 4,401,116 A | 8/1983 | Fry et al. |
| 4,417,573 A | 11/1983 | De |
| 4,425,914 A | 1/1984 | Ray et al. |
| 4,449,990 A | 5/1984 | Tedford, Jr. |
| 4,450,838 A | 5/1984 | Miodownik |
| 4,459,982 A | 7/1984 | Fry |
| 4,502,481 A | 3/1985 | Christian |
| 4,502,873 A | 3/1985 | Mottram et al. |
| 4,516,424 A | 5/1985 | Rowland |
| 4,527,557 A | 7/1985 | Devries et al. |
| 4,545,790 A | 10/1985 | Miller et al. |
| 4,561,287 A | 12/1985 | Rowland |
| 4,576,616 A | 3/1986 | Mottram et al. |
| 4,602,653 A | 7/1986 | Ruiz-vela et al. |
| 4,621,632 A | 11/1986 | Bartels et al. |
| 4,627,860 A | 12/1986 | Rowland |
| 4,637,386 A | 1/1987 | Baum |
| 4,648,395 A | 3/1987 | Sato et al. |
| 4,648,888 A | 3/1987 | Rowland |
| 4,681,099 A | 7/1987 | Sato et al. |
| 4,682,591 A | 7/1987 | Jones |
| 4,702,240 A | 10/1987 | Chaoui |
| 4,794,922 A | 1/1989 | Devries |
| 4,807,616 A | 2/1989 | Adahan |
| 4,813,979 A | 3/1989 | Miller et al. |
| 4,869,733 A | 9/1989 | Stanford |
| 4,880,443 A | 11/1989 | Miller et al. |
| 4,905,685 A | 3/1990 | Olsson et al. |
| 4,936,297 A | 6/1990 | Greiff et al. |
| 4,941,469 A | 7/1990 | Adahan |
| 4,971,609 A | 11/1990 | Pawlos |
| 4,983,190 A | 1/1991 | Verrando et al. |
| 4,993,269 A | 2/1991 | Guillaume et al. |
| 5,002,591 A | 3/1991 | Stanford |
| 5,014,694 A | 5/1991 | Devries |
| 5,021,137 A | 6/1991 | Joshi et al. |
| 5,024,219 A | 6/1991 | Dietz |
| 5,034,023 A | 7/1991 | Thompson |
| 5,071,453 A | 12/1991 | Hradek et al. |
| 5,072,729 A | 12/1991 | Devries |
| 5,101,656 A | 4/1992 | Miller |
| 5,107,831 A | 4/1992 | Halpern et al. |
| 5,127,400 A | 7/1992 | Devries et al. |
| 5,129,924 A | 7/1992 | Schultz |
| 5,134,329 A | 7/1992 | Lang |
| 5,161,525 A | 11/1992 | Kimm et al. |
| 5,166,563 A | 11/1992 | Bassine |
| 5,169,506 A | 12/1992 | Michaels |
| 5,186,793 A | 2/1993 | Michaels |
| 5,265,594 A | 11/1993 | Olsson et al. |
| 5,273,031 A | 12/1993 | Olsson et al. |
| 5,275,642 A | 1/1994 | Bassine |
| 5,296,110 A | 3/1994 | Tabatabaie-Raissi |
| 5,331,995 A | 7/1994 | Westfall et al. |
| 5,335,426 A | 8/1994 | Settlemyer et al. |
| 5,354,361 A | 10/1994 | Coffield |
| 5,370,112 A | 12/1994 | Perkins |
| 5,378,345 A | 1/1995 | Taylor et al. |
| 5,397,443 A | 3/1995 | Michaels |
| 5,400,777 A | 3/1995 | Olsson et al. |
| 5,469,372 A | 11/1995 | Mcbrearty et al. |
| 5,474,062 A | 12/1995 | Devires et al. |
| 5,474,595 A | 12/1995 | Mccombs |
| 5,494,028 A | 2/1996 | Devries et al. |
| 5,497,767 A | 3/1996 | Olsson et al. |
| 5,501,212 A | 3/1996 | Psaros |
| 5,540,220 A | 7/1996 | Gropper et al. |
| 5,540,233 A | 7/1996 | Larsson et al. |
| 5,575,283 A | 11/1996 | Sjoestrand |
| 5,578,115 A | 11/1996 | Cole |
| 5,676,133 A | 10/1997 | Hickle et al. |
| 5,694,924 A | 12/1997 | Cewers |
| 5,694,926 A | 12/1997 | Devries et al. |
| 5,701,883 A | 12/1997 | Hete et al. |
| 5,706,801 A | 1/1998 | Remes et al. |
| 5,720,277 A | 2/1998 | Olsson et al. |
| 5,740,796 A | 4/1998 | Skog |
| 5,743,253 A | 4/1998 | Castor et al. |
| 5,746,806 A | 5/1998 | Aylsworth et al. |
| 5,765,557 A | 6/1998 | Warters |
| 5,765,558 A | 6/1998 | Psaros et al. |
| 5,766,310 A | 6/1998 | Cramer |
| 5,810,324 A | 9/1998 | Eriksson et al. |
| 5,827,358 A | 10/1998 | Kulish et al. |
| 5,845,633 A | 12/1998 | Psaros |
| 5,849,219 A | 12/1998 | De et al. |
| 5,858,062 A | 1/1999 | Mcculloh et al. |
| 5,858,063 A | 1/1999 | Cao et al. |
| 5,862,802 A | 1/1999 | Bird |
| 5,868,133 A | 2/1999 | Devries et al. |
| 5,871,564 A | 2/1999 | Mccombs |
| 5,875,777 A | 3/1999 | Eriksson |
| 5,878,744 A | 3/1999 | Pfeiffer |
| 5,881,722 A | 3/1999 | Devries et al. |
| 5,893,944 A | 4/1999 | Dong |
| 5,896,857 A | 4/1999 | Hely et al. |
| 5,906,672 A | 5/1999 | Michaels et al. |
| 5,917,135 A | 6/1999 | Michaels et al. |
| 5,931,162 A | 8/1999 | Christian |
| 5,937,853 A | 8/1999 | Stroem |
| 5,948,142 A | 9/1999 | Holmes et al. |
| 5,957,130 A | 9/1999 | Krahbichler et al. |
| 5,968,236 A | 10/1999 | Bassine |
| 5,988,165 A | 11/1999 | Richey, II et al. |
| 5,997,617 A | 12/1999 | Czabala et al. |
| 6,010,555 A | 1/2000 | Smolarek et al. |
| 6,035,851 A | 3/2000 | Wallen |
| 6,062,218 A | 5/2000 | Krahbichler et al. |
| 6,068,680 A | 5/2000 | Kulish et al. |
| 6,073,630 A | 6/2000 | Adahan |
| 6,095,139 A | 8/2000 | Psaros |
| 6,102,038 A | 8/2000 | Devries |
| 6,112,744 A | 9/2000 | Hoegnelid |
| 6,113,673 A | 9/2000 | Loutfy et al. |
| 6,123,074 A | 9/2000 | Hete et al. |
| 6,152,132 A | 11/2000 | Psaros |
| 6,152,134 A | 11/2000 | Webber et al. |
| 6,152,135 A | 11/2000 | Devries et al. |

(56) References Cited

U.S. PATENT DOCUMENTS

| | | | |
|---|---|---|---|
| 6,155,252 A | 12/2000 | Warters |
| 6,156,100 A | 12/2000 | Conrad et al. |
| 6,158,430 A | 12/2000 | Pfeiffer et al. |
| 6,162,283 A | 12/2000 | Conrad et al. |
| 6,176,897 B1 | 1/2001 | Keefer |
| 6,186,142 B1 | 2/2001 | Schmidt et al. |
| 6,189,532 B1 | 2/2001 | Hely et al. |
| 6,190,441 B1 | 2/2001 | Czabala et al. |
| 6,192,885 B1 | 2/2001 | Jalde |
| 6,217,635 B1 | 4/2001 | Conrad et al. |
| 6,234,170 B1 | 5/2001 | Bergkvist |
| 6,253,767 B1 | 7/2001 | Mantz |
| 6,263,873 B1 | 7/2001 | Hedenberg |
| 6,269,811 B1 | 8/2001 | Duff |
| 6,298,848 B1 | 10/2001 | Skog |
| 6,302,107 B1 | 10/2001 | Richey, II et al. |
| 6,344,069 B2 | 2/2002 | Smolarek et al. |
| 6,346,139 B1 | 2/2002 | Czabala |
| 6,348,082 B1 | 2/2002 | Murdoch et al. |
| 6,360,740 B1 | 3/2002 | Ward et al. |
| 6,386,235 B1 | 5/2002 | Mcculloh et al. |
| 6,393,802 B1 | 5/2002 | Bowser et al. |
| 6,394,089 B1 | 5/2002 | Cantrill et al. |
| 6,395,065 B1 | 5/2002 | Murdoch et al. |
| 6,412,483 B1 | 7/2002 | Jones et al. |
| 6,446,630 B1 | 9/2002 | Todd, Jr. |
| 6,471,744 B1 | 10/2002 | Hill |
| 6,478,850 B2 | 11/2002 | Warren |
| 6,478,857 B2 | 11/2002 | Czabala |
| 6,497,755 B2 | 12/2002 | Murdoch et al. |
| 6,514,318 B2 | 2/2003 | Keefer |
| 6,514,319 B2 | 2/2003 | Keefer et al. |
| 6,516,798 B1 | 2/2003 | Davies |
| 6,520,176 B1 | 2/2003 | Dubois et al. |
| 6,524,370 B2 | 2/2003 | Maheshwary et al. |
| 6,526,970 B2 | 3/2003 | Devries et al. |
| 6,532,956 B2 | 3/2003 | Hill |
| 6,547,851 B2 | 4/2003 | Warren |
| 6,551,384 B1 | 4/2003 | Ackley et al. |
| 6,553,992 B1 | 4/2003 | Berthon-jones et al. |
| 6,558,451 B2 | 5/2003 | Mccombs et al. |
| 6,564,798 B1 | 5/2003 | Jalde |
| 6,565,635 B2 | 5/2003 | Keefer et al. |
| 6,581,594 B1 | 6/2003 | Drew et al. |
| 6,595,213 B2 | 7/2003 | Bennarsten |
| 6,601,583 B2 | 8/2003 | Pessala et al. |
| 6,622,726 B1 | 9/2003 | Du |
| 6,626,175 B2 | 9/2003 | Jafari et al. |
| 6,629,525 B2 | 10/2003 | Hill et al. |
| 6,640,807 B2 | 11/2003 | Bennarsten |
| 6,641,644 B2 | 11/2003 | Jagger et al. |
| 6,641,645 B1 | 11/2003 | Lee et al. |
| 6,644,312 B2 | 11/2003 | Berthon-Jones et al. |
| 6,651,652 B1 | 11/2003 | Waard |
| 6,651,658 B1 | 11/2003 | Hill et al. |
| 6,651,692 B2 | 11/2003 | Meckes et al. |
| 6,660,065 B2 | 12/2003 | Byrd et al. |
| 6,668,828 B1 | 12/2003 | Figley et al. |
| 6,679,258 B1 | 1/2004 | Stroem |
| 6,691,702 B2 | 2/2004 | Appel et al. |
| 6,694,978 B1 | 2/2004 | Bennarsten |
| 6,702,880 B2 | 3/2004 | Roberts et al. |
| 6,712,876 B2 | 3/2004 | Cao et al. |
| 6,712,877 B2 | 3/2004 | Cao et al. |
| 6,739,334 B2 | 5/2004 | Valeij |
| 6,740,146 B2 | 5/2004 | Simonds |
| 6,755,193 B2 | 6/2004 | Berthon-jones et al. |
| 6,758,216 B1 | 7/2004 | Berthon-jones et al. |
| 6,761,166 B2 | 7/2004 | Ahlmen et al. |
| 6,764,534 B2 | 7/2004 | Mccombs et al. |
| 6,782,888 B1 | 8/2004 | Friberg et al. |
| 6,793,719 B2 | 9/2004 | Kim et al. |
| 6,805,122 B2 | 10/2004 | Richey, II et al. |
| 6,811,590 B2 | 11/2004 | Lee et al. |
| 6,837,244 B2 | 1/2005 | Yagi et al. |
| 6,845,773 B2 | 1/2005 | Berthon-jones et al. |
| 6,860,858 B2 | 3/2005 | Green et al. |
| 6,863,068 B2 | 3/2005 | Jamison et al. |
| 6,866,700 B2 | 3/2005 | Amann |
| 6,877,511 B2 | 4/2005 | Devries et al. |
| 6,889,726 B2 | 5/2005 | Richey, II et al. |
| 6,896,721 B1 | 5/2005 | Lynn |
| 6,908,503 B2 | 6/2005 | Mccombs et al. |
| 6,910,480 B1 | 6/2005 | Berthon-jones |
| 6,923,180 B2 | 8/2005 | Richey, II et al. |
| 6,935,460 B2 | 8/2005 | Mccombs et al. |
| 6,949,133 B2 | 9/2005 | Mccombs et al. |
| 6,997,881 B2 | 2/2006 | Green et al. |
| 7,000,610 B2 | 2/2006 | Bennarsten et al. |
| 7,032,592 B2 | 4/2006 | Castor et al. |
| 7,040,318 B2 | 5/2006 | Daescher et al. |
| 7,055,522 B2 | 6/2006 | Berthon-jones |
| 7,066,985 B2 | 6/2006 | Deane et al. |
| 7,077,133 B2 | 7/2006 | Yagi et al. |
| 7,081,745 B2 | 7/2006 | Haveri |
| 7,089,937 B2 | 8/2006 | Berthon-jones et al. |
| 7,094,275 B2 | 8/2006 | Keefer et al. |
| 7,096,866 B2 | 8/2006 | Be'eri et al. |
| 7,100,609 B2 | 9/2006 | Berthon-jones et al. |
| 7,105,038 B2 | 9/2006 | Lee et al. |
| 7,121,276 B2 | 10/2006 | Jagger et al. |
| 7,121,277 B2 | 10/2006 | Stroem |
| 7,135,059 B2 | 11/2006 | Deane et al. |
| 7,156,903 B2 | 1/2007 | Mccombs |
| 7,171,963 B2 | 2/2007 | Jagger et al. |
| 7,179,326 B2 | 2/2007 | Nakamura et al. |
| 7,188,621 B2 | 3/2007 | DeVries et al. |
| 7,213,468 B2 | 5/2007 | Fujimoto |
| 7,219,666 B2 | 5/2007 | Friberg et al. |
| 7,222,623 B2 | 5/2007 | Devries et al. |
| 7,250,073 B2 | 7/2007 | Keefer et al. |
| 7,255,103 B2 | 8/2007 | Bassin |
| 7,279,029 B2 | 10/2007 | Occhialini et al. |
| 7,294,170 B2 | 11/2007 | Richey, II et al. |
| 7,318,437 B2 | 1/2008 | Gunaratnam et al. |
| 7,329,304 B2 | 2/2008 | Bliss et al. |
| 7,347,207 B2 | 3/2008 | Ahlmen et al. |
| 7,350,521 B2 | 4/2008 | Whitley et al. |
| 7,367,337 B2 | 5/2008 | Berthon-jones et al. |
| 7,368,005 B2 | 5/2008 | Bliss et al. |
| RE40,402 E | 6/2008 | Leonhardt et al. |
| 7,402,193 B2 | 7/2008 | Bliss et al. |
| 7,406,966 B2 | 8/2008 | Wondka |
| 7,427,315 B2 | 9/2008 | Dolensky et al. |
| 7,428,902 B2 | 9/2008 | Du et al. |
| 7,429,289 B2 | 9/2008 | Dolensky et al. |
| 7,431,032 B2 | 10/2008 | Jagger et al. |
| 7,438,745 B2 | 10/2008 | Deane et al. |
| 7,445,546 B2 | 11/2008 | Hondmann et al. |
| 7,445,663 B1 | 11/2008 | Hunter et al. |
| 7,455,717 B2 | 11/2008 | Sprinkle |
| 7,473,299 B2 | 1/2009 | Occhialini et al. |
| 7,491,261 B2 | 2/2009 | Warren et al. |
| 7,497,215 B1 | 3/2009 | Nguyen et al. |
| 7,510,601 B2 | 3/2009 | Whitley et al. |
| 7,517,385 B2 | 4/2009 | Winter |
| 7,524,365 B2 | 4/2009 | Lin |
| 7,527,053 B2 | 5/2009 | Devries et al. |
| 7,533,872 B2 | 5/2009 | Lee et al. |
| 7,550,031 B2 | 6/2009 | Hunter et al. |
| 7,550,036 B2 | 6/2009 | Lee et al. |
| 7,556,670 B2 | 7/2009 | Aylsworth et al. |
| 7,559,326 B2 | 7/2009 | Smith et al. |
| 7,585,351 B2 | 9/2009 | Deane et al. |
| 7,590,551 B2 | 9/2009 | Auer |
| 7,604,004 B2 | 10/2009 | Jagger et al. |
| 7,604,005 B2 | 10/2009 | Jagger et al. |
| 7,628,151 B2 | 12/2009 | Bassin |
| 7,637,989 B2 | 12/2009 | Bong |
| 7,655,059 B2 | 2/2010 | Wang et al. |
| 7,655,063 B2 | 2/2010 | Wang et al. |
| 7,682,428 B2 | 3/2010 | Nawata et al. |
| 7,682,429 B2 | 3/2010 | Dolensky et al. |
| 7,686,870 B1 | 3/2010 | Deane et al. |

(56) References Cited

U.S. PATENT DOCUMENTS

| | | |
|---|---|---|
| 7,704,304 B2 | 4/2010 | Warren et al. |
| 7,708,802 B1 | 5/2010 | Deane et al. |
| 7,708,818 B2 | 5/2010 | Clark |
| 7,717,981 B2 | 5/2010 | Labuda et al. |
| 7,722,700 B2 | 5/2010 | Sprinkle |
| 7,727,160 B2 | 6/2010 | Green et al. |
| 7,730,887 B2 | 6/2010 | Deane et al. |
| 7,753,996 B1 | 7/2010 | Deane et al. |
| 7,758,672 B2 | 7/2010 | Lee et al. |
| 7,763,103 B2 | 7/2010 | Dolensky et al. |
| 7,766,010 B2 | 8/2010 | Jagger et al. |
| 7,771,511 B2 | 8/2010 | Dolensky |
| 7,780,768 B2 | 8/2010 | Taylor et al. |
| 7,780,769 B2 | 8/2010 | Dolensky et al. |
| 7,794,522 B2 | 9/2010 | Bliss et al. |
| 7,828,878 B2 | 11/2010 | Zhong et al. |
| 7,837,761 B2 | 11/2010 | Bliss et al. |
| 7,841,343 B2 | 11/2010 | Deane et al. |
| 7,849,854 B2 | 12/2010 | Devries et al. |
| 7,857,894 B2 | 12/2010 | Taylor et al. |
| 7,861,716 B2 | 1/2011 | Borrello |
| 7,866,315 B2 | 1/2011 | Jagger et al. |
| 7,874,290 B2 | 1/2011 | Chalvignac |
| 7,875,105 B2 | 1/2011 | Chambers et al. |
| 7,892,322 B2 | 2/2011 | Ono et al. |
| 7,909,034 B2 | 3/2011 | Sinderby et al. |
| 7,914,459 B2 | 3/2011 | Green et al. |
| 7,918,925 B2 | 4/2011 | Dolensky et al. |
| 7,922,789 B1 | 4/2011 | Deane et al. |
| 7,934,499 B2 | 5/2011 | Berthon-jones |
| 7,954,493 B2 | 6/2011 | Nawata |
| 8,006,692 B2 | 8/2011 | Smith et al. |
| 8,016,916 B2 | 9/2011 | Ono et al. |
| 8,016,918 B2 | 9/2011 | Labuda et al. |
| 8,016,925 B2 | 9/2011 | Mccombs et al. |
| 8,020,553 B2 | 9/2011 | Jagger et al. |
| 8,051,852 B2 | 11/2011 | Bassin |
| 8,062,003 B2 | 11/2011 | Goertzen |
| 8,070,853 B2 | 12/2011 | Sprinkle |
| 8,070,864 B2 | 12/2011 | Uchiyama et al. |
| 8,070,922 B2 | 12/2011 | Nelson et al. |
| 8,075,676 B2 | 12/2011 | Thompson et al. |
| 8,100,125 B2 | 1/2012 | Duquette et al. |
| 8,118,024 B2 | 2/2012 | Devries et al. |
| 8,122,885 B2 | 2/2012 | Berthon-jones et al. |
| 8,123,497 B2 | 2/2012 | Richey, II et al. |
| 8,142,544 B2 | 3/2012 | Taylor et al. |
| 8,146,596 B2 | 4/2012 | Smith et al. |
| 8,147,597 B2 | 4/2012 | Dolensky et al. |
| 8,156,937 B2 | 4/2012 | Devries et al. |
| 8,167,988 B2 | 5/2012 | Dolensky et al. |
| 8,192,526 B2 | 6/2012 | Zhong et al. |
| 8,210,205 B2 | 7/2012 | Michaels |
| 8,225,789 B2 | 7/2012 | Berthon-jones |
| 8,226,745 B2 | 7/2012 | Siew-wah et al. |
| 8,236,095 B1 | 8/2012 | Bassine |
| 8,256,419 B2 | 9/2012 | Sinderby et al. |
| 8,257,473 B2 | 9/2012 | Mccombs et al. |
| 8,280,498 B2 | 10/2012 | Jalde |
| 8,282,717 B2 | 10/2012 | Chambers et al. |
| 8,297,279 B2 | 10/2012 | Devries et al. |
| 8,337,599 B2 | 12/2012 | Kiritake |
| 8,343,259 B2 | 1/2013 | Knaebel |
| 8,349,053 B2 | 1/2013 | Lee et al. |
| 8,361,204 B1 | 1/2013 | Bassine |
| 8,366,815 B2 | 2/2013 | Taylor et al. |
| 8,371,298 B2 | 2/2013 | Hallback et al. |
| 8,375,944 B2 | 2/2013 | Kwok |
| 8,377,180 B2 | 2/2013 | Maeda et al. |
| 8,377,181 B2 | 2/2013 | Taylor et al. |
| 8,388,548 B2 | 3/2013 | Green et al. |
| 8,388,745 B1 | 3/2013 | Pelletier et al. |
| 8,400,290 B2 | 3/2013 | Baker, Jr. |
| 8,418,691 B2 | 4/2013 | Jafari et al. |
| 8,418,692 B2 | 4/2013 | Sanchez |
| 8,424,520 B2 | 4/2013 | Thiessen |
| 8,424,521 B2 | 4/2013 | Jafari et al. |
| 8,428,672 B2 | 4/2013 | Sherman et al. |
| 8,434,480 B2 | 5/2013 | Jafari et al. |
| 8,434,482 B2 | 5/2013 | Borrello |
| 8,434,488 B2 | 5/2013 | Li et al. |
| 8,435,013 B2 | 5/2013 | Kondou et al. |
| 8,440,004 B2 | 5/2013 | Taylor et al. |
| 8,443,294 B2 | 5/2013 | Skidmore et al. |
| 8,448,640 B2 | 5/2013 | Bassin |
| 8,448,641 B2 | 5/2013 | Jafari et al. |
| 8,469,026 B2 | 6/2013 | Blomberg et al. |
| 8,522,780 B2 | 9/2013 | Devries et al. |
| 8,539,952 B2 | 9/2013 | Carbone et al. |
| 8,627,819 B2 | 1/2014 | Devries et al. |
| 8,683,997 B2 | 4/2014 | Devries et al. |
| 8,770,191 B2 | 7/2014 | Tham |
| 8,844,530 B2 | 9/2014 | Bimkrant |
| 9,126,002 B2 | 9/2015 | Devries et al. |
| 9,345,851 B2 | 5/2016 | Kim et al. |
| 9,504,799 B2 | 11/2016 | Hardin et al. |
| 9,522,248 B2 | 12/2016 | Martin |
| 9,956,371 B2 | 5/2018 | DeVries |
| 10,046,134 B2 | 8/2018 | DeVries |
| 10,105,509 B2 | 10/2018 | DeVries |
| 10,245,406 B2 | 4/2019 | Devries |
| 10,315,002 B2 | 6/2019 | Devries et al. |
| 10,350,377 B2 | 7/2019 | Fiorenza |
| 10,518,059 B2 | 12/2019 | Cipollone et al. |
| 10,758,699 B2 | 9/2020 | Cipollone et al. |
| 10,773,049 B2 | 9/2020 | Gaw et al. |
| 11,191,915 B2 | 12/2021 | Ahmad |
| 2002/0005197 A1 | 1/2002 | DeVries |
| 2002/0053286 A1 | 5/2002 | Czabala |
| 2002/0092420 A1 | 7/2002 | Jagger et al. |
| 2002/0121278 A1 | 9/2002 | Hete |
| 2003/0000531 A1 | 1/2003 | Tuck |
| 2003/0010208 A1 | 1/2003 | Jagger et al. |
| 2003/0024766 A1 | 2/2003 | Briscoe |
| 2003/0051729 A1 | 3/2003 | Be et al. |
| 2003/0111077 A1 | 6/2003 | Hooser |
| 2003/0131848 A1 | 7/2003 | Stenzler |
| 2003/0196550 A1 | 10/2003 | Keefer et al. |
| 2003/0200865 A1 | 10/2003 | Mccombs et al. |
| 2003/0230308 A1 | 12/2003 | Linden |
| 2004/0021108 A1 | 2/2004 | Hallback et al. |
| 2004/0060560 A1 | 4/2004 | Stenzler et al. |
| 2004/0231913 A1 | 11/2004 | Mccombs et al. |
| 2005/0012657 A1 | 1/2005 | Mohan |
| 2005/0045040 A1 | 3/2005 | Mccombs |
| 2005/0072298 A1 | 4/2005 | Deane et al. |
| 2005/0072306 A1 | 4/2005 | Deane et al. |
| 2005/0072423 A1 | 4/2005 | Deane et al. |
| 2005/0072426 A1 | 4/2005 | Deane et al. |
| 2005/0103341 A1 | 5/2005 | Deane et al. |
| 2005/0112013 A1 | 5/2005 | Devries et al. |
| 2005/0217481 A1 | 10/2005 | Dunne et al. |
| 2005/0257686 A1 | 11/2005 | Occhialini et al. |
| 2005/0274381 A1 | 12/2005 | Deane et al. |
| 2005/0274815 A1 | 12/2005 | Bergholtz et al. |
| 2006/0011065 A1 | 1/2006 | Hastings |
| 2006/0042631 A1 | 3/2006 | Martin et al. |
| 2006/0064802 A1 | 3/2006 | Damrath et al. |
| 2006/0086251 A1 | 4/2006 | Sprinkle |
| 2006/0102181 A1 | 5/2006 | Mccombs et al. |
| 2006/0107947 A1 | 5/2006 | Rist |
| 2006/0117957 A1 | 6/2006 | Mccombs et al. |
| 2006/0137522 A1 | 6/2006 | Nishimura et al. |
| 2006/0144240 A1 | 7/2006 | Lee et al. |
| 2006/0174871 A1 | 8/2006 | Jagger et al. |
| 2006/0174875 A1 | 8/2006 | Jagger et al. |
| 2006/0174877 A1 | 8/2006 | Jagger et al. |
| 2006/0230924 A1 | 10/2006 | Deane et al. |
| 2006/0230929 A1 | 10/2006 | Bliss et al. |
| 2006/0230931 A1 | 10/2006 | Bliss et al. |
| 2006/0230939 A1 | 10/2006 | Bliss et al. |
| 2006/0266357 A1 | 11/2006 | Mccombs et al. |
| 2006/0283325 A1 | 12/2006 | Sugano |
| 2006/0283447 A1 | 12/2006 | Dhuper et al. |

(56) References Cited

U.S. PATENT DOCUMENTS

| | | |
|---|---|---|
| 2007/0031302 A1 | 2/2007 | Wittrup et al. |
| 2007/0056583 A1 | 3/2007 | Jagger et al. |
| 2007/0056584 A1 | 3/2007 | Jagger et al. |
| 2007/0084342 A1 | 4/2007 | Hunter et al. |
| 2007/0084349 A1 | 4/2007 | Calkins et al. |
| 2007/0101999 A1 | 5/2007 | Duquette et al. |
| 2007/0135757 A1 | 6/2007 | Acker |
| 2007/0144521 A1 | 6/2007 | Devries et al. |
| 2007/0148016 A1 | 6/2007 | Crawford et al. |
| 2007/0169623 A1 | 7/2007 | Lee et al. |
| 2007/0199566 A1 | 8/2007 | Be |
| 2007/0214955 A1 | 9/2007 | Aylsworth et al. |
| 2007/0227360 A1 | 10/2007 | Atlas et al. |
| 2007/0227540 A1 | 10/2007 | Ljungberg et al. |
| 2007/0272243 A1 | 11/2007 | Sherman et al. |
| 2007/0289446 A1 | 12/2007 | Occhialini et al. |
| 2008/0000477 A1 | 1/2008 | Huster et al. |
| 2008/0004566 A1 | 1/2008 | Sloan |
| 2008/0028933 A1 | 2/2008 | Ross et al. |
| 2008/0034975 A1 | 2/2008 | Chambers et al. |
| 2008/0053441 A1 | 3/2008 | Gottlib |
| 2008/0066616 A1 | 3/2008 | Sprinkle |
| 2008/0066741 A1 | 3/2008 | LeMahieu et al. |
| 2008/0087170 A1 | 4/2008 | Deane et al. |
| 2008/0092892 A1 | 4/2008 | Boyle et al. |
| 2008/0092893 A1 | 4/2008 | Boyle et al. |
| 2008/0110338 A1 | 5/2008 | Taylor et al. |
| 2008/0110451 A1 | 5/2008 | Dunsmore et al. |
| 2008/0110461 A1 | 5/2008 | Mulqueeny et al. |
| 2008/0135044 A1 | 6/2008 | Freitag et al. |
| 2008/0185544 A1 | 8/2008 | Yeh |
| 2008/0196580 A1 | 8/2008 | Bliss et al. |
| 2008/0202337 A1 | 8/2008 | Taylor et al. |
| 2008/0202508 A1 | 8/2008 | Mcclain et al. |
| 2008/0251071 A1 | 10/2008 | Armitstead et al. |
| 2008/0257145 A1 | 10/2008 | Sprinkle et al. |
| 2008/0257349 A1 | 10/2008 | Hedner et al. |
| 2008/0282880 A1 | 11/2008 | Bliss et al. |
| 2008/0295839 A1 | 12/2008 | Habashi |
| 2008/0302362 A1 | 12/2008 | Kwok |
| 2008/0302363 A1 | 12/2008 | Kroupa |
| 2008/0314385 A1 | 12/2008 | Brunner et al. |
| 2008/0315441 A1 | 12/2008 | Lee et al. |
| 2009/0007912 A1 | 1/2009 | Lindell et al. |
| 2009/0025560 A1 | 1/2009 | Takemasa |
| 2009/0025564 A1 | 1/2009 | Kuwabara |
| 2009/0044698 A1 | 2/2009 | Meacham |
| 2009/0065007 A1 | 3/2009 | Wilkinson et al. |
| 2009/0065526 A1 | 3/2009 | Sprinkle |
| 2009/0071333 A1 | 3/2009 | Labuda et al. |
| 2009/0078251 A1 | 3/2009 | Zucchi et al. |
| 2009/0084381 A1 | 4/2009 | Devries et al. |
| 2009/0101147 A1 | 4/2009 | Landis et al. |
| 2009/0107500 A1 | 4/2009 | Edwards |
| 2009/0133368 A1 | 5/2009 | Calkins et al. |
| 2009/0133694 A1 | 5/2009 | Solci et al. |
| 2009/0145428 A1 | 6/2009 | Sward et al. |
| 2009/0167698 A1 | 7/2009 | Altas et al. |
| 2009/0188502 A1 | 7/2009 | Tiedje |
| 2009/0211448 A1 | 8/2009 | Mcclain |
| 2009/0229459 A1 | 9/2009 | Warren et al. |
| 2009/0250059 A1 | 10/2009 | Allum et al. |
| 2009/0301477 A1 | 12/2009 | Pierro et al. |
| 2009/0308396 A1 | 12/2009 | Mcclain |
| 2010/0024819 A1 | 2/2010 | Tiedje |
| 2010/0051030 A1 | 3/2010 | Richard et al. |
| 2010/0052293 A1 | 3/2010 | Brooks et al. |
| 2010/0071693 A1 | 3/2010 | Allum et al. |
| 2010/0078018 A1 | 4/2010 | Heinonen |
| 2010/0095841 A1 | 4/2010 | Naheiri |
| 2010/0116270 A1 | 5/2010 | Branson et al. |
| 2010/0122699 A1 | 5/2010 | Birkrant |
| 2010/0126249 A1 | 5/2010 | Matsuzaki |
| 2010/0154797 A1 | 6/2010 | Landis et al. |
| 2010/0229867 A1 | 9/2010 | Bertinetti et al. |
| 2010/0275921 A1 | 11/2010 | Schindhelm et al. |
| 2010/0282084 A1 | 11/2010 | Hansen et al. |
| 2010/0288279 A1 | 11/2010 | Seiver et al. |
| 2010/0294127 A1 | 11/2010 | Dolensky |
| 2011/0000489 A1 | 1/2011 | Laksov et al. |
| 2011/0030684 A1 | 2/2011 | Wilkinson et al. |
| 2011/0030685 A1 | 2/2011 | Wilkinson et al. |
| 2011/0030686 A1 | 2/2011 | Wilkinson et al. |
| 2011/0030687 A1 | 2/2011 | Wilkinson et al. |
| 2011/0030689 A1 | 2/2011 | Wilkinson et al. |
| 2011/0057651 A1 | 3/2011 | Duric et al. |
| 2011/0067699 A1 | 3/2011 | Caruso et al. |
| 2011/0073107 A1 | 3/2011 | Rodman et al. |
| 2011/0073115 A1 | 3/2011 | Wood et al. |
| 2011/0113964 A1 | 5/2011 | Chambers et al. |
| 2011/0154986 A1 | 6/2011 | Lee et al. |
| 2011/0192122 A1 | 8/2011 | Whitesel et al. |
| 2011/0197882 A1 | 8/2011 | Truschel et al. |
| 2011/0197883 A1 | 8/2011 | Mcdaniel et al. |
| 2011/0197884 A1 | 8/2011 | Duff et al. |
| 2011/0197887 A1 | 8/2011 | Truschel et al. |
| 2011/0197889 A1 | 8/2011 | Lahde et al. |
| 2011/0209706 A1 | 9/2011 | Truschel et al. |
| 2011/0209707 A1 | 9/2011 | Terhark |
| 2011/0220107 A1 | 9/2011 | Kimm et al. |
| 2011/0232483 A1 | 9/2011 | Haberland et al. |
| 2011/0232645 A1 | 9/2011 | Smith |
| 2011/0247616 A1 | 10/2011 | Von et al. |
| 2011/0247620 A1 | 10/2011 | Armstrong et al. |
| 2011/0247621 A1 | 10/2011 | Richard et al. |
| 2011/0247622 A1 | 10/2011 | Schneider et al. |
| 2011/0259334 A1 | 10/2011 | Alfieri et al. |
| 2011/0297153 A1 | 12/2011 | Grimsey |
| 2011/0303223 A1 | 12/2011 | Kane et al. |
| 2011/0315140 A1 | 12/2011 | Shuman |
| 2012/0000462 A1 | 1/2012 | Edwards et al. |
| 2012/0006199 A1 | 1/2012 | Mccombs et al. |
| 2012/0006326 A1 | 1/2012 | Ahmad |
| 2012/0012109 A1 | 1/2012 | Chalvignac |
| 2012/0017909 A1 | 1/2012 | Porges et al. |
| 2012/0027628 A1 | 2/2012 | Ogawa |
| 2012/0037159 A1 | 2/2012 | Mulqueeny et al. |
| 2012/0055340 A1 | 3/2012 | Wilkinson et al. |
| 2012/0055474 A1 | 3/2012 | Wilkinson |
| 2012/0055475 A1 | 3/2012 | Wilkinson |
| 2012/0055477 A1 | 3/2012 | Wilkinson |
| 2012/0055480 A1 | 3/2012 | Wilkinson |
| 2012/0055482 A1 | 3/2012 | Wilkinson |
| 2012/0055483 A1 | 3/2012 | Wilkinson et al. |
| 2012/0060840 A1 | 3/2012 | Refsland et al. |
| 2012/0125336 A1 | 5/2012 | Berthon-jones et al. |
| 2012/0125337 A1 | 5/2012 | Asanoi |
| 2012/0152248 A1 | 6/2012 | Richey, II et al. |
| 2012/0167883 A1 | 7/2012 | Taylor et al. |
| 2012/0167886 A1 | 7/2012 | Taylor et al. |
| 2012/0167887 A1 | 7/2012 | Taylor et al. |
| 2012/0167888 A1 | 7/2012 | Taylor et al. |
| 2012/0174926 A1 | 7/2012 | Tham |
| 2012/0177546 A1 | 7/2012 | Hilbig |
| 2012/0192862 A1 | 8/2012 | Lewis et al. |
| 2012/0192864 A1 | 8/2012 | Galbraith et al. |
| 2012/0192867 A1 | 8/2012 | Lewis et al. |
| 2012/0247329 A1 | 10/2012 | Hilbig |
| 2012/0266883 A1 | 10/2012 | Taylor et al. |
| 2012/0285460 A1 | 11/2012 | Smith et al. |
| 2012/0285543 A1 | 11/2012 | Michaels |
| 2012/0291884 A1 | 11/2012 | Yamaura et al. |
| 2012/0304867 A1 | 12/2012 | Watanabe et al. |
| 2012/0308779 A1 | 12/2012 | Klee et al. |
| 2012/0318145 A1 | 12/2012 | Hilbig et al. |
| 2013/0008438 A1 | 1/2013 | Sugawara et al. |
| 2013/0008444 A1 | 1/2013 | Chalvignac et al. |
| 2013/0025591 A1 | 1/2013 | Clark et al. |
| 2013/0031784 A1 | 2/2013 | Chambers et al. |
| 2013/0032148 A1 | 2/2013 | Neely |
| 2013/0081617 A1 | 4/2013 | Cavendish |
| 2013/0087145 A1 | 4/2013 | Koebrich et al. |
| 2013/0087146 A1 | 4/2013 | Callaghan et al. |
| 2013/0092159 A1 | 4/2013 | Ulrichskoetter et al. |

(56) References Cited

U.S. PATENT DOCUMENTS

| | | |
|---|---|---|
| 2013/0098361 A1 | 4/2013 | Koebrich et al. |
| 2013/0104898 A1 | 5/2013 | Berthon-Jones |
| 2013/0125891 A1 | 5/2013 | Eddy |
| 2013/0167843 A1 | 7/2013 | Kimm et al. |
| 2013/0186400 A1 | 7/2013 | Jafari et al. |
| 2013/0186401 A1 | 7/2013 | Jafari et al. |
| 2013/0199520 A1 | 8/2013 | Dhuper et al. |
| 2013/0220325 A1 | 8/2013 | Davis et al. |
| 2013/0255689 A1 | 10/2013 | Kim et al. |
| 2013/0272905 A1 | 10/2013 | Shelke |
| 2013/0276789 A1 | 10/2013 | Garde et al. |
| 2013/0312757 A1 | 11/2013 | Gragg et al. |
| 2014/0007878 A1 | 1/2014 | Armistead et al. |
| 2014/0116441 A1 | 5/2014 | Mcdaniel |
| 2014/0150789 A1 | 6/2014 | Flanagan et al. |
| 2014/0150791 A1 | 6/2014 | Birnkrant et al. |
| 2014/0150792 A1 | 6/2014 | Christopher et al. |
| 2014/0166009 A1 | 6/2014 | Flanagan et al. |
| 2014/0216446 A1 | 8/2014 | Wruck |
| 2014/0283834 A1 | 9/2014 | Ahmad et al. |
| 2014/0318535 A1 | 10/2014 | Bullock |
| 2014/0373835 A1 | 12/2014 | Ahmad et al. |
| 2015/0000654 A1 | 1/2015 | Martin |
| 2015/0000660 A1 | 1/2015 | Martin |
| 2015/0027444 A1 | 1/2015 | Col, Jr. |
| 2015/0101610 A1 | 4/2015 | Nitta |
| 2015/0224278 A1 | 8/2015 | Addington et al. |
| 2015/0283352 A1 | 10/2015 | Karkkainen |
| 2015/0320962 A1 | 11/2015 | Bafile |
| 2016/0095997 A1 | 4/2016 | Kapust et al. |
| 2016/0129213 A1 | 5/2016 | Zhu et al. |
| 2016/0243330 A1 | 8/2016 | Destefano |
| 2016/0279369 A1 | 9/2016 | Cipollone |
| 2016/0279378 A1 | 9/2016 | Cipollone et al. |
| 2017/0000968 A1 | 1/2017 | Harrington et al. |
| 2017/0361058 A1 | 12/2017 | Gaw et al. |
| 2018/0085541 A1 | 3/2018 | Ye et al. |
| 2019/0054268 A1 | 2/2019 | DeVries |
| 2019/0344033 A1 | 11/2019 | Ahmad |
| 2021/0252243 A1 | 8/2021 | Barlow et al. |

FOREIGN PATENT DOCUMENTS

| | | |
|---|---|---|
| CN | 201065977 Y | 5/2008 |
| CN | 201240850 Y | 5/2009 |
| CN | 201273451 Y | 7/2009 |
| CN | 101765443 A | 6/2010 |
| CN | 101962125 A | 2/2011 |
| CN | 102300599 A | 12/2011 |
| CN | 102500030 A | 6/2012 |
| CN | 103071215 A | 5/2013 |
| CN | 203943984 U | 11/2014 |
| CN | 203988387 U | 12/2014 |
| CN | 204307184 U | 5/2015 |
| CN | 204917961 U | 12/2015 |
| CN | 112587771 A | 4/2021 |
| CN | 112587772 A | 4/2021 |
| EP | 0937478 B1 | 8/2003 |
| GB | 2164568 A | 3/1986 |
| GB | 2485417 A | 5/2012 |
| JP | 59116041 A | 7/1984 |
| JP | H11-192410 A | 7/1999 |
| JP | H11-210927 A | 8/1999 |
| JP | 2000024110 A | 1/2000 |
| JP | 2000102617 A | 4/2000 |
| JP | 2000300673 A | 10/2000 |
| JP | 2001120660 A | 5/2001 |
| JP | 2001507982 A | 6/2001 |
| JP | 2002136598 A | 5/2002 |
| JP | 2003156174 A | 5/2003 |
| JP | 2007117273 A | 5/2007 |
| JP | 2008501445 A | 1/2008 |
| JP | 2008539841 A | 11/2008 |
| JP | 2010535078 A | 11/2010 |
| JP | 2012508074 A | 4/2012 |
| JP | 201418030 A | 9/2014 |
| JP | 2015080699 A | 4/2015 |
| KR | 20130123640 A | 11/2013 |
| WO | 1998022172 A | 5/1998 |
| WO | 9826830 A | 6/1998 |
| WO | 1999008738 A1 | 2/1999 |
| WO | 0038772 A1 | 7/2000 |
| WO | 2003008017 A2 | 1/2003 |
| WO | 2003045486 A1 | 6/2003 |
| WO | 2004004815 A1 | 1/2004 |
| WO | 2005025658 A1 | 3/2005 |
| WO | 2006102345 A1 | 9/2006 |
| WO | 2006121980 A2 | 11/2006 |
| WO | 2009105597 A1 | 8/2009 |
| WO | 2010054323 A3 | 5/2010 |
| WO | 2010058308 A2 | 5/2010 |
| WO | 2010141983 A1 | 12/2010 |
| WO | 2011161060 A1 | 12/2011 |
| WO | 2012052903 A1 | 4/2012 |
| WO | 2013033589 A1 | 3/2013 |
| WO | 2013067592 A1 | 5/2013 |
| WO | 2013140321 A1 | 9/2013 |
| WO | 2013164733 A1 | 11/2013 |
| WO | 2014059405 A1 | 4/2014 |
| WO | 2014089188 A1 | 6/2014 |
| WO | 2014135997 A1 | 9/2014 |
| WO | 2014176454 A1 | 10/2014 |
| WO | 2015015394 A1 | 2/2015 |
| WO | 2015126853 A1 | 8/2015 |
| WO | 2015192186 A1 | 12/2015 |
| WO | 2016067147 A1 | 5/2016 |
| WO | 2017149532 A1 | 9/2017 |
| WO | 2019191814 A1 | 10/2019 |

OTHER PUBLICATIONS

Branson, D R. et al., Branson, D. Richard et al., "Maximizing Oxygen Delivery During Mechanical Ventilation with a Portable Oxygen Concentrator," The Journal of Trauma® Injury, Infection, and Critical Care, vol. 69, No. 1, July Supplement 2010, 7 pages., Jul. 2010, 7 pages.

Extended European Search Report mailed Sep. 24, 2018 in European Patent Application No. 16769634.3, 7 pages.

Gandidine et al., "System Design Verification for Closed Loop Control of Oxygenation With Concentrator Integration," Military Medicine, 2016, vol. 181(5):177-183.

Gustafson, et al., Gustafson et al., "Pulse Dose Delivery of Oxygen in Mechanically Ventilated Pigs with Acute Lung Injury," The Journal of Trauma and Acute Care Surgery, 75(5), Nov. 2013, pp. 775-779., 5 pages.

International Search Report and Written Opinion mailed Jun. 10, 2016 in International Patent Application No. PCT/US2016/023828, 11 pages.

Rodriguez et al., "Maximizing Oxygen Delivery During Mechanical Ventilation with a Portable Oxygen Concentrator," Journal of Trauma-Injury Infection & Critical Care, 69(1), Jul. 2020, pp. S87-S93.

International Search Report and Written Opinion mailed Aug. 8, 2019 in International Patent Application No. PCT/US2019/027094, 13 pages.

European Extended Search Report mailed Dec. 16, 2021 in EP19804599. 9, 9 pages.

Canadian Office Action mailed Jan. 12, 2023 in Canadian Patent Application No. 2,980,306, 5 pages.

International Search Report and Written Opinion mailed Mar. 17, 2022 in International Patent Application No. PCT/US2021/064722, 12 pages.

International Search Report and Written Opinion mailed Aug. 2, 2022 in International Patent Application No. PCT/US2022/071677, 19 pages.

Japanese Office Action with translation mailed Feb. 13, 2023 in Japanese Patent No. 2021-514284, 13 pages.

Chinese Office Action (Notice of Allowance) with English translation mailed Apr. 28, 2024 in Chinese Patent Application No. 202011330634.5, 7 pages.

(56) References Cited

OTHER PUBLICATIONS

Chinese Office Action with English translation mailed Apr. 20, 2024 in Chinese Patent Application No. 202011442606.2, 9 pages.
Chinese Office Action with English translation mailed Jul. 27, 2024 in Chinese Patent Application No. 202011387869.8, 16 pages.
Chinese Office Action with English translation mailed Mar. 16, 2024 in Chinese Patent Application No. 202011387876.8, 23 pages.
Japanese Office Action with English translation mailed Nov. 13, 2023 in Japanese Patent Application No. 2021-514284, 8 pages.
Japanese Office Action with translation mailed Oct. 3, 2024 in Japanese Patent Application No. 2023-76384, 6 pages.
Extended European Search Report mailed on Oct. 8, 2024 in European Patent Application No. 21912087.0, 11 pages.

PORTABLE MEDICAL VENTILATOR SYSTEM USING PORTABLE OXYGEN CONCENTRATORS

CROSS-REFERENCE TO RELATED APPLICATION

This application is a continuation of U.S. patent application Ser. No. 16/381,897, filed Apr. 11, 2019, which claims priority to U.S. Provisional Patent Application No. 62/670,856, filed May 13, 2018, under 35 U.S.C. 119, and both of which are incorporated by reference herein.

TECHNICAL FIELD

The present invention relates, in general, to medical ventilators, and, in particular, to portable ventilators that improve the fraction of inspired oxygen values by integrating a negative pressure triggering device in the ventilator to trigger a pulse flow and/or multiple pulses from an oxygen concentrator.

BACKGROUND

Oxygen is normally supplied to portable ventilators by high flow oxygen concentrators with constant oxygen flow, compressed gas cylinders, or fixed medical oxygen plumbing systems. The oxygen is mixed with air within the ventilator to supply a desired fraction of inspired oxygen (FIO2) to the patient so as to efficiently treat a medical condition. When such high-pressure sources are unavailable or limited in capacity, low pressure, low flow oxygen is supplied to ventilators using oxygen concentrators, which typically delivers 1-10 LPM oxygen by mixing air and oxygen at either the input or the outlet of the blower or compressor.

In the past, oxygen has been added to the inspiratory limb of the patient's breathing circuit prior to the inspiration cycle. The oxygen-rich gas stored in the inspiratory limb is preferentially delivered to the patient when a breath is delivered by the ventilator. The inspiratory limb's proximal location in the ventilator circuit results in an elevated fraction of inspired oxygen within the alveolar space of the patient's lungs. In all cases, the current state of the art ventilators uses only low, continuous flow settings of oxygen from the concentrator or other oxygen delivery device. This method can only be used with continues flow concentrators and cannot be used with triggered oxygen concentrators.

A concentrator has been connected to the inlet of the ventilator's compressor. This volume of oxygen, plus the air delivered by the ventilator, combines to make a homogenous mixture which is then delivered to a patient to yield a fraction of inspired oxygen within the patient's lungs. In this type of configuration, the ventilator cannot trigger a concentrator and can only use a fix flow concentrator.

Portable oxygen concentrators, compressed gas cylinders, and liquid oxygen storage devices are also used to provide supplemental oxygen to respiratory patients via nasal cannula for the purposes of increasing the fraction of inspired oxygen. In these cases, oxygen delivery is either a low continuous flow or a pulsed flow triggered by a decrease in pressure in the cannula as the patient inhales. This method does not provide any mechanical ventilation to the patient.

Taken alone, these prior art methods are capable of producing fractions of inspired oxygen for the patient sufficient enough to treat some medical conditions while the patient is at home or near a high oxygen flow source. When traditional high-pressure or high-flow sources of oxygen are not available, not economical, or need to be conserved, there is a need for systems and techniques that improve FIO2 values while conserving oxygen and energy beyond the methods that are currently available.

Prior art methods can produce fractions of inspired oxygen from a pulse concentrator by modifying the concentrator to accept a signal from the ventilator. However, there is a need for a portable ventilator to be used with all unmodified concentrators and still be able to deliver the oxygen to the nasal pillows interface needed to increase the FIO2 of the patient.

Prior art methods are capable of producing FIO2 from a pulse concentrator by modifying the patient circuit to include a Venturi valve or Venturi tube to generate a negative pressure that triggers the oxygen concentrator. These methods require a higher pressure and/or flow from the portable ventilator so that the Venturi can generate the negative pressure needed to trigger the concentrator. Portable ventilators have low pressure and low flow, so they cannot be used with Venturi which requires higher pressure and/or flow to be able to generate negative pressure. Also, the Venturi will leak air at low pressure and/or flow which will reduce the flow and/or pressure to the patient. Using these methods, FIO2 will be low since the oxygen pulse is mixed with the flow of the ventilator and some of this mixed flow will leak at the patient interface. There is a need for portable ventilators to be used with all unmodified pulse concentrators and still be able to deliver higher FIO2 to the patient by bypassing the leak of the patient circuit and the patient interface.

These prior art methods are not effective when used for portable ventilator with a portable pulse concentrator. Portable ventilators are limited in pressure and/or flow and they implement a high level of leaks at the interface, therefore the fractions of inspired oxygen will not be effective when portable pulse concentrators are used. There is a need for a portable ventilator that can trigger any pulse oxygen concentrator and deliver the oxygen pulse to the patient interface directly and bypass the leak ports in the patient interface and circuit.

The invention possesses numerous benefits and advantages over known portable ventilators. In particular, the invention utilizes a method to trigger any portable oxygen concentrator that uses triggered pulse delivery mechanism. Moreover, the oxygen pulse is delivered directly to the patient interface and bypasses any leaks in the patient circuit or patient interface. Because of this invention, patients who require lighter equipment can be outside for an extended time while being portable and receiving higher FIO2.

SUMMARY

According to an aspect of this invention, a ventilator system, similar to ventilators commonly used in conjunction with nasal pillows interface is connected to the patient breathing circuit of a portable ventilator. The portable ventilator is capable of triggering a pulse of oxygen from a portable oxygen concentrator and deliver the oxygen pulse directly to the patient interface. In one embodiment, the ventilator is designed to trigger any portable concentrator when a negative pressure is generated in the ventilator. The negative pressure is connected to the concentrator and triggers the concentrator to deliver the oxygen pulse to the patient interface. In other embodiments, an electromechanical negative pressure device is placed in the ventilator to generate a negative pressure at any time during ventilation and the negative pressure is used to trigger the concentrator to distribute a pulse and/or pulses of oxygen to the patient during inhalation and/or exhalation.

An additional aspect of the invention involves the design of nasal canals inside the pillows interface and a method of delivering the oxygen pulse to the patient directly and by bypassing the potential leaks in the patient circuit and the interface. The delivery of the oxygen to the patient is facilitated by a ventilator circuit that connects the ventilator to the patient using multi-tubes or multi-lumen tube. The multi-tubes or multi-lumen tube includes an air delivery line that is used during the inhalation and the exhalation cycles. The multi-tubes or multi-lumen tube also includes a pulsed oxygen delivery line and pressure sensing and/or patient monitoring line.

One or more implementations of the aspect of the invention described immediately above include one or more of the following: delivering a continuous flow rate of oxygen to the oxygen cannula inside the nasal pillows interface; triggering the oxygen source for pulsed delivery of a bolus of oxygen; triggering the oxygen source includes triggering the oxygen source based upon the start of inspiratory phase and/or at any point during the inspiratory and/or exhalation phase; triggering the oxygen source includes triggering the oxygen concentrator using an electro-mechanical negative pressure device at that location inside the ventilator; generating the negative pressure within the ventilator multiple times during inhalation and/or exhalation to trigger the oxygen source. Triggering the oxygen source includes the microprocessor, in the ventilator, sending a signal to the electro-mechanical negative pressure device to generate a negative pressure that is detected by the portable concentrator to deliver the pulsed delivery of a bolus of oxygen. A triggering event causes the triggering of the oxygen source for oxygen bolus delivery, and the time for the triggering event is set by the user to be at the beginning of inspiration or anytime during inspiration/exhalation. The triggering method of the POC, using a negative pressure device, is not affected by positive end expiratory pressure (PEEP) and the method is not affected by ventilator bias flow; due to using a check-valve downstream of the negative pressure device.

Another aspect of the invention involves a medical ventilator system that increases the fraction of inspired oxygen delivered to a patient nasal pillows interface using multi-tubes or multi-lumen patient circuit tube. The medical ventilator system includes: A positive pressure blower for delivering a breath to the patient during an inspiration cycle and controlling pressure during an exhalation cycle; an electro-mechanical negative pressure device to trigger the POC; a multi-tubes or multi-lumen patient circuit for connecting the ventilator to the patient and the patient circuit including an air flow delivery line, an oxygen delivery line, and a pressure sensing and/or monitoring line; the ventilator triggering mechanism for detecting the patient effort is based on flow or pressure sensors integrated in the ventilator.

One or more implementations of the aspect of the invention described immediately above include one or more of the following: the ventilator mechanism includes a sensor that senses a positive inspiratory pressure at the patient and located in the nasal pillows interface; the triggering mechanism of the ventilator includes a flow sensor and/or pressure sensor in location inside the ventilator; the ventilator includes the oxygen source triggering mechanism, and the triggering mechanism is in communication with the oxygen source for pulsed delivery of a bolus of oxygen; the triggering mechanism triggers the oxygen source by generating a negative pressure which triggers the oxygen source; a ventilator triggering event causes the triggering mechanism to trigger the oxygen source for oxygen bolus delivery; and a triggering of the negative pressure is synchronized by the microprocessor of the ventilator and set by the user to trigger the pulse or pulses at any set time of the breath.

Another aspect of the invention involves a system for at least one of increasing fraction of inspired oxygen delivered by a medical ventilator via a ventilator multi-tubes or multi-lumen circuit and delivered to the patient's nostrils through the oxygen cannula within the nasal pillows interface. Also, the ventilator circuit includes means to deliver pressurized air to the patient through the nasal pillows and to measure pressure proximal to the patient. The medical ventilator system includes an oxygen source triggering mechanism; a verbal speed blower; negative pressure device for triggering the oxygen source for pulsed delivery of a bolus of oxygen to the patient from the ventilator to location proximal to the patient nostrils or interface to increase fraction of inspired oxygen delivered to the patient.

One or more implementations of the aspect of the invention described immediately above include one or more of the following: the ventilator delivers a continuous flow rate of air to the patient circuit; the triggering mechanism includes a sensor that senses a patient trigger effort; the triggering mechanism includes a negative pressure device located in the ventilator; the ventilator includes the triggering mechanism which sends a negative pneumatic signal to the oxygen source for pulsed delivery of a bolus of oxygen; the ventilator circuit includes separate lines for the delivery of the pressurized air to the patient, oxygen delivery, and pressure sensing and/or monitoring.

A further aspect of the invention involves a portable medical ventilator that allows the use of pulse flow from an oxygen concentrator to gain higher oxygen concentration. The ventilator includes both a positive pressure source to deliver pressurized air to the patient and a negative pressure source to trigger the oxygen concentrator. A patient circuit attached to a nasal pillows interface mask connects the ventilator to the patient. The ventilator includes a controller module that is configured to generate a signal to the negative pressure device to trigger the concentrator to initiate one or more pulses of oxygen from the oxygen concentrator. The oxygen pulses are delivered to the patient nasal pillows interface or to the patient interface directly through multi-tubes or a multi lumen patient circuit. The oxygen does not mix with air in the ventilator or in the patient circuit. The nasal pillows interface or the patient interface includes an oxygen nasal cannula (or oxygen connection tube) to deliver the pulses of oxygen directly to the chamber of the pillows (or the nasal pillows interface). The activation of the negative pressure source initiated by the microprocessor and can be configured by the user of the ventilator. The portable medical ventilator works with any portable concentrator.

A still further aspect of the invention involves a medical ventilator for delivering a pressurized breath to a patient and to trigger an oxygen source to increase FiO2 delivered to the patient comprising a ventilation delivery interface including one or more mixing chambers; a positive pressure source; a negative pressure source; a ventilator circuit for connecting the ventilator to the ventilation delivery interface, the ventilator circuit including a multiple lumen circuit to deliver pressurized air and pulsed oxygen upon triggering of the pressurized breath, wherein the ventilation delivery interface includes a first lumen and a second lumen, the first lumen being an air delivery lumen to deliver air to the one or more mixing chambers, and the second lumen being an oxygen delivery lumen to deliver oxygen to the one or more mixing chambers to mix with the air just prior to delivery to the patient and bypassing any interface leaks without mixing previously in the ventilator nor the ventilator circuit.

One or more implementations of the aspect of the invention described immediately above include one or more of the following: the oxygen source delivers a continuous flow rate of oxygen to the ventilator; the oxygen source is a pulsed oxygen concentrator that delivers pulses of a bolus of oxygen to the ventilator; the ventilator is configured to trigger the oxygen source by generating a negative pressure in the ventilator at any time during patient inspiration and exhalation; the ventilator is configured so that the negative pressure source causes multiple triggering of the oxygen source for oxygen bolus delivery during inspiration; the ventilation delivery interface is a member selected from the group consisting of one or more intubation tubes, a non-rebreather mask, a partial rebreather mask, a full face mask, a total face mask, a nasal cannula, and a nasal pillow; and/or the ventilation delivery interface further includes a third lumen, which is at least one of triggering lumen and a monitoring lumen.

Another aspect of the invention involves a method for delivering a pressurized breath to a patient and to trigger an oxygen source to increase FiO2 delivered to the patient with the medical ventilator described immediately above, comprising triggering delivery of the first medical gas and the second medical gas with the third lumen; and mixing the first medical gas and the second medical gas in the one or more mixing chambers of the ventilation delivery interface just prior to delivery to the patient and bypassing any interface leaks without mixing previously in the ventilator nor the ventilator circuit.

An additional aspect of the invention involves a nasal pillows interface for delivery of multiple gases to a patient comprising pillows to seal at nostrils of the patient to deliver pressurized mixed medical gases; one or more mixing chambers; a first lumen, a second lumen, the first lumen being a first medical gas delivery lumen to deliver a first medical gas to the patient, the second lumen being a second medical gas delivery lumen to deliver a second medical gas to the patient, wherein the first lumen and the second lumen are configured to deliver the first medical gas and the second medical gas to the one or more mixing chambers to mix the first medical gas and the second medical gas just prior to delivery to the patient and bypassing any interface leaks without mixing previously in the ventilator nor the ventilator circuit.

One or more implementations of the aspect of the invention described immediately above include one or more of the following: the first lumen is an air delivery lumen to deliver air to the patient, the second lumen is an oxygen delivery lumen to deliver oxygen to the patient, and the first lumen and the second lumen are configured to deliver the air and the oxygen to the one or more mixing chambers to mix the air and the oxygen just prior to delivery to the patient and bypassing any interface leaks without mixing previously in the ventilator nor the ventilator circuit; and/or one or more mixing chambers include respective mixing chambers in the pillows.

Another aspect of the invention involves a method for delivering multiple gases to a patient with the nasal pillows of aspect of the invention described immediately above, wherein the nasal pillows interface includes a third lumen, which is at least one of triggering lumen and a monitoring lumen, the method comprising triggering delivery of the first medical gas and the second medical gas with the third lumen; and mixing the first medical gas and the second medical gas in the one or more mixing chambers of the nasal pillows interface just prior to delivery to the patient and bypassing any interface leaks without mixing previously in the ventilator nor the ventilator circuit.

One or more implementations of the aspect of the invention described immediately above include one or more of the following: the ventilator includes a ventilator internal triggering flow sensor, the method comprising triggering delivery of the first medical gas and the second medical gas with the ventilator internal triggering flow sensor; mixing the first medical gas and the second medical gas in the one or more mixing chambers of the nasal pillows interface just prior to delivery to the patient and bypassing any interface leaks without mixing previously in the ventilator nor the ventilator circuit; and/or the one or more mixing chambers include respective mixing chambers in the pillows.

A further aspect of the invention involves a ventilation delivery interface for delivery of multiple gases from a ventilator circuit and ventilator to a patient, comprising one or more mixing chambers; a first lumen and a second lumen, the first lumen being a first medical gas delivery lumen to deliver a first medical gas to the patient, the second lumen being a second medical gas delivery lumen to deliver a second medical gas to the patient, wherein the first lumen and the second lumen are configured to deliver the first medical gas and the second medical gas to the one or more mixing chambers to mix the first medical gas and the second medical gas just prior to delivery to the patient and bypassing any interface leaks without mixing previously in the ventilator nor the ventilator circuit.

One or more implementations of the aspect of the invention described immediately above include one or more of the following: the ventilation delivery interface is a member selected from the group consisting of one or more intubation tubes, a non-rebreather mask, a partial rebreather mask, a full face mask, a total face mask, a nasal cannula, nasal mask, and a nasal pillow; and/or a third lumen being at least one of triggering lumen and a monitoring lumen.

A still further aspect of the invention involves a method for delivering a pressurized breath to a patient and to trigger an oxygen source to increase FiO2 delivered to the patient with the ventilation delivery interface described immediately above, comprising triggering delivery of the first medical gas and the second medical gas with the triggering lumen; and mixing the first medical gas and the second medical gas in the one or more mixing chambers of the ventilation delivery interface just prior to delivery to the patient and bypassing any interface leaks without mixing previously in the ventilator nor the ventilator circuit.

A still further aspect of the invention involves a method for delivering a pressurized breath to a patient and to trigger an oxygen source to increase FiO2 delivered to the patient with the ventilation delivery interface described immediately above, wherein the ventilator includes a ventilator internal triggering flow sensor, the method comprising triggering delivery of the first medical gas and the second medical gas with the ventilator internal triggering flow sensor; and mixing the first medical gas and the second medical gas in the one or more mixing chambers of the ventilation delivery interface just prior to delivery to the patient and bypassing any interface leaks without mixing previously in the ventilator nor the ventilator circuit.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein.

DETAILED DESCRIPTION

The subject matter described herein is taught by way of example implementations. Various details have been omitted for the sake of clarity and to avoid obscuring the subject matter. The examples shown below are directed to devices, apparatus and methods for increasing the fraction of inspired oxygen (FIO2) to a patient. Other features and advantages of the subject matter should be apparent from the following description.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation.

The terminology used herein is for describing particular embodiments only and is not intended to be limiting of the invention. As such, this detailed description of various alternative embodiments should not be construed to limit the scope or breadth of the present invention.

A system and method for increasing the fraction of inspired oxygen (FIO2) to a patient or user (e.g., spontaneously breathing patient, non-spontaneously breathing patient) in a medical ventilator that uses pulse flow rather than continuous flow of oxygen from low pressure oxygen sources such as the oxygen concentrators described. Other oxygen sources such as oxygen concentrators, compressed oxygen tanks, membrane oxygen generators, chemical oxygen generators, liquid oxygen systems, or any oxygen delivery system that requires patient effort to initiate the delivery of the oxygen pulse and/or flow could be used in the same manner.

Figure 1:
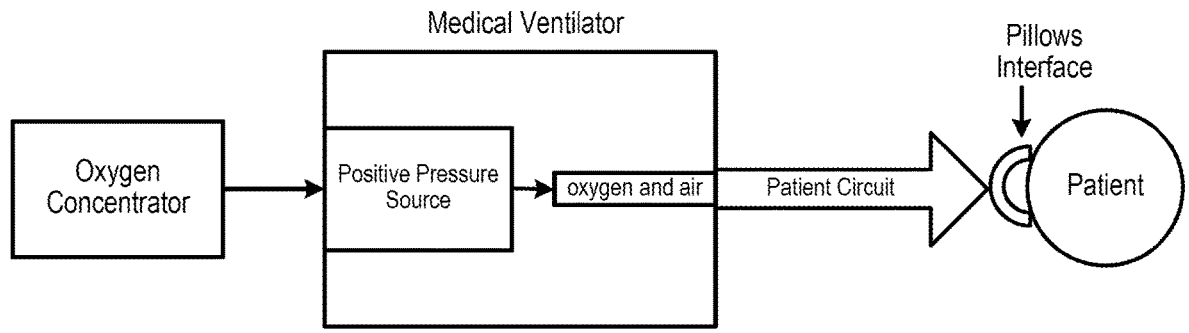
FIG. 1 illustrates one example of a typical prior art medical ventilator system where the oxygen concentrator is connected to the inlet of the ventilator blower.

FIG. 1 illustrates a typical prior art medical ventilator 20. The medical ventilator 20 includes a positive pressure source 30, patient circuit 40 for supplying mixed oxygen and air to a user and pillows user interface 50 and portable oxygen source 70.

Conditions of the medical ventilator 20 such as flow rate, oxygen concentration level, etc. may be constant for the system, may be manually controllable, and/or may be automatically controllable. For example, the medical ventilator 20 may include a user interface that allows the user, provider, doctor, etc. to enter information, e.g., prescription oxygen level, flow rate, etc. to control the oxygen output of the ventilator system 10. A flow of oxygen mixed with air is distributed from the medical ventilator 20 to the patient during each breath via breathing or user circuit 40 in the inspiration phase, and the flow is discontinued during the exhalation phase. It should be noted that some ventilators have a small flow rate during exhalation phase used to maintain a positive pressure during exhalation so in those instances flow is not completely discontinued during the exhalation phase. A small continuous flow rate of oxygen can be added during this phase too.

The control module of the ventilator 20 may take any well-known form in the art and includes a central microprocessor or CPU that communicates with the components of the ventilator 20 described herein via one or more interfaces, controllers, or other electrical circuit elements for controlling and managing the medical ventilator 40. The ventilator system 20 may include a user interface as a part of the control module 60 or coupled to the control module for allowing the user, provider, doctor, etc. to enter information, e.g., prescription oxygen level, flow rate, activity level, etc., to control the ventilator.

Figure 2:
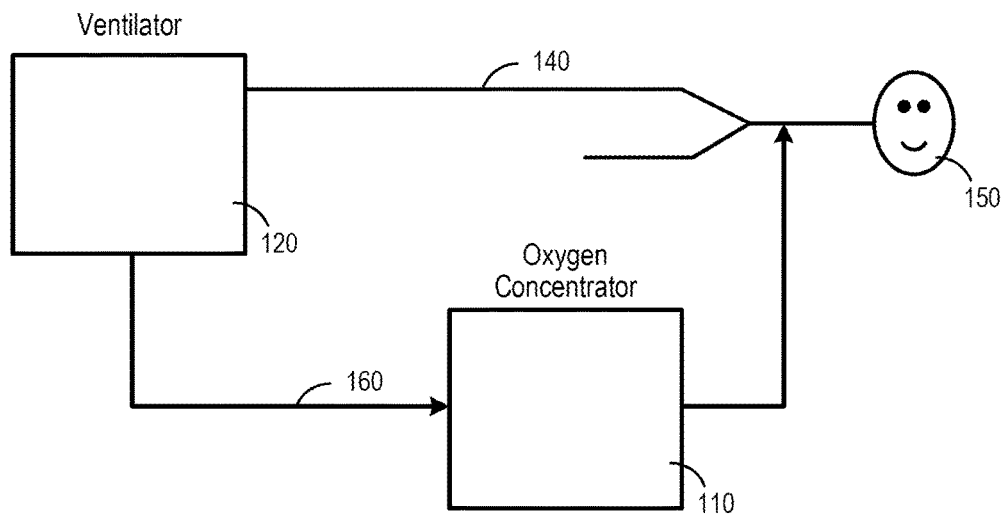
FIG. 2 illustrates one example of a typical prior art medical ventilator system where a signal connects the oxygen concentrator and the medical ventilator.

FIG. 2 illustrates a prior art medical ventilator system including an oxygen source (e.g., oxygen concentrator/conserving device) 110, a medical ventilator 120 and a breathing circuit 140 between the ventilator 120 and a patient 150. In one embodiment, the oxygen concentrator 110 includes a controller/control module (e.g., controller that processed one or more modules stored in memory perform the function(s) described herein) that is configured to generate a trigger signal 160 to initiate the distribution of pulses of oxygen (or a pulse bolus of oxygen) from the oxygen concentrator 110. In some embodiments, a conserving device may be used in conjunction with the oxygen concentrator 110 to control the distribution of oxygen to the breathing circuit 140. In other embodiments, the conserving device can be independent of the oxygen concentrator 110. The controller module for generating a trigger signal to initiate the distribution of pulses of oxygen from the oxygen concentrator 110 can be incorporated in the oxygen concentrator 110 and/or the conserving device. In this prior art, the oxygen concentrator needs to be modified to accept a triggering signal from the ventilator.

Figure 3:
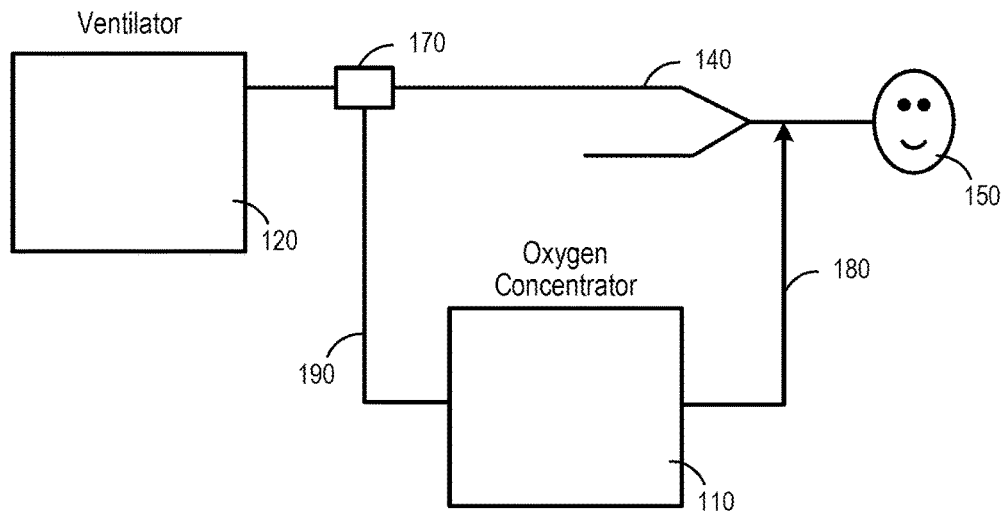
FIG. 3 illustrates one example of a typical prior art medical ventilator where a Venturi is added in the patient circuit to trigger the oxygen concentrator.

FIG. 3 illustrates a prior art medical ventilator system including an oxygen source (e.g., oxygen concentrator/conserving device) 110, a medical ventilator 120 and a breathing circuit 140 between the ventilator 120 and a patient 150. In one embodiment, the oxygen concentrator 110 connects to the negative port of a Venturi 170 which is located in the breathing circuit 140. The Venturi 170 is configured to generate a negative pressure which is connected to the concentrator to initiate the distribution of a pulse of oxygen (or a pulse bolus of oxygen) from the oxygen concentrator 110. The patient circuit need to be modified to include the Venturi 170. The Venturi 170 requires higher pressure and/or flow than pressures and/or flows generated by a potable ventilator. One pulse can be delivered by the concentrator using this method which will reduce the FIO2. When using a BI-Level ventilation method or PEEP during exhalation, the Venturi will generate a negative pressure during the inhalation and exhalation cycles which will cause the concentrator to miss triggering and therefore reduce the FIO2 to the patient.

Figure 4:
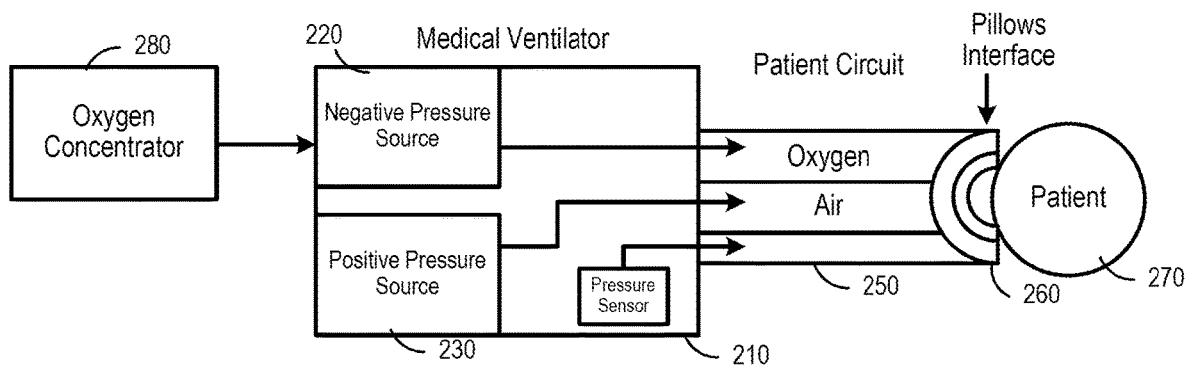
FIG. 4 illustrates an embodiment of a medical ventilator.

With reference to FIG. 4, an embodiment of a medical ventilator 210 will be described. The medical ventilator 210 includes a positive pressure source 230 to generate air flow that creates positive pressure at the patient and negative pressure source 220 to generate a negative pressure that triggers an oxygen source (e.g., oxygen concentrator) 280. The medical ventilator 210 is connected to a patient/breathing circuit 250 with multi-tubes or multi-lumen tube. The multi-lumen tube contains three lumens, one for the ventilator pressurized air, one for the oxygen flow and one for pressure sensing. The breathing circuit 250 is connected to pillows interface 260 which is connected to the patient 270. The ventilator 210 can be used with any oxygen concentrators 280 currently used to provide oxygen to ambulatory patients via a nasal cannula. The triggering of the pulses of the oxygen by the oxygen concentrator 280 is controlled by the negative pressure device within the ventilator 210. The negative pressure can be generated to start the oxygen pulse or pulses during the inspiration cycle and/or during exhalation cycle.

The patient/breathing circuit 250 includes a special connector to the medical ventilator. The breathing circuit 250 includes three tubes or a three-lumen tube: 1) an air pressurized gas, 2) an oxygen flow and/or pulses, and 3) a pressure sensing line. The three tubes or the three-lumen tube are connected to the nasal pillows interface 260.

The negative pressure device 220 generates negative pressure in the ventilator 210 which triggers the concentrator 280 to deliver a pulse of oxygen to the ventilator oxygen inlet. The pulse of oxygen will be delivered directly to the oxygen cannula in the nasal pillows interface 260 through the patient/breathing circuit 250.

In another embodiment, a small continuous flow of oxygen may also be supplied when a pulse is not being delivered to aid in elevating FIO2.

In one embodiment, the oxygen concentrator 280 supplies pulse flow to the ventilator 210 to gain higher FIO2 values. The medical ventilator 210 may include one or more output sensors to sense one or more conditions of the user 270, pressure, flow, leak, respiratory rate, activity environment, etc. to monitor the patient while ventilated.

Figure 5:
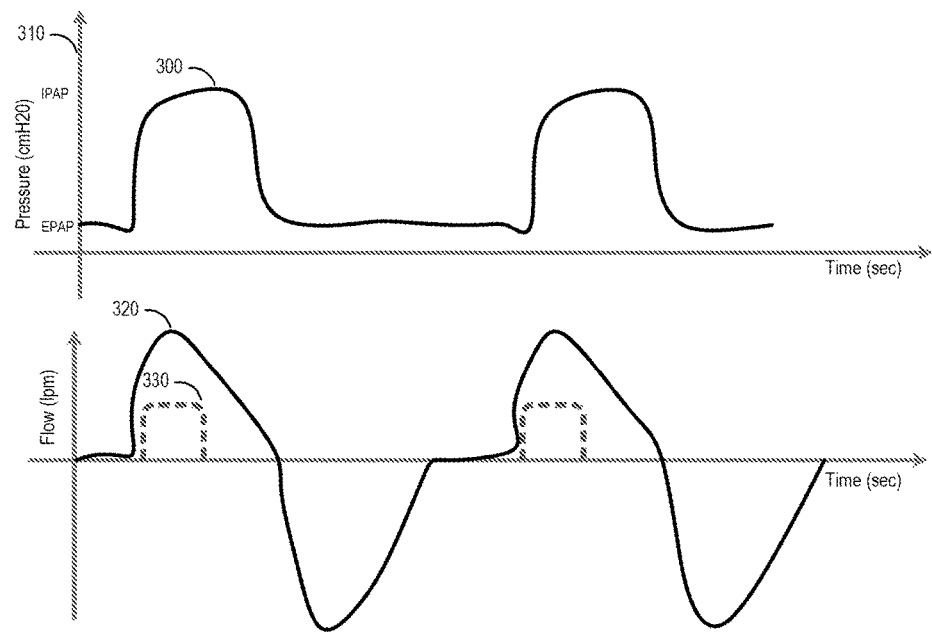
FIG. 5 is an example graph illustrating a method of delivering one oxygen pulse during the inspiratory time.

FIG. 5 illustrates one example of a waveform graph identifying the patient pressure signal 300 and air flow 320 and one oxygen pulse 330 delivered by the concentrator to the ventilator 330. The x-axis represents the time in seconds in the patient or breathing circuit and the y-axis represents pressure in cm H2O 310. In one embodiment, the ventilator air flow 320 is shown, and one oxygen pulse is shown in the same graph 330

Figure 6:
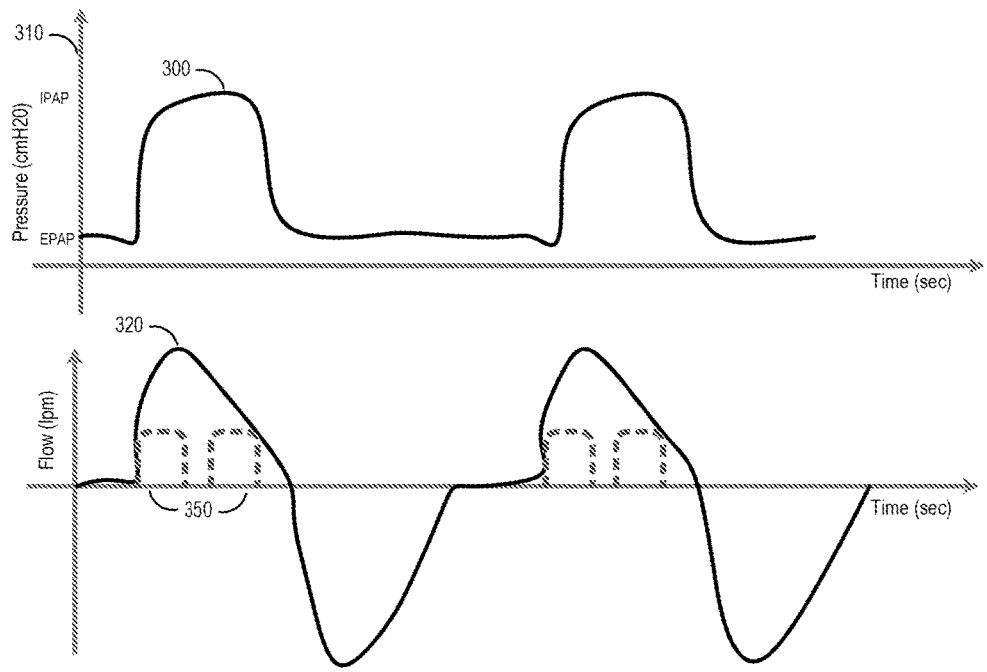
FIG. 6 is an example graph illustrating a method of delivering multiple oxygen pulses during the inspiratory time.

FIG. 6 illustrates one example of a waveform graph identifying the patient pressure signal 300 and air flow 320 and multiple oxygen pulses 350 delivered by the ventilator. The x-axis represents the time in seconds in the patient or breathing circuit 250 and the y-axis represents pressure in cmH2O 310. In one embodiment, the ventilator air flow 320, and two oxygen pulses 350 are shown in the same graph.

Figure 7:
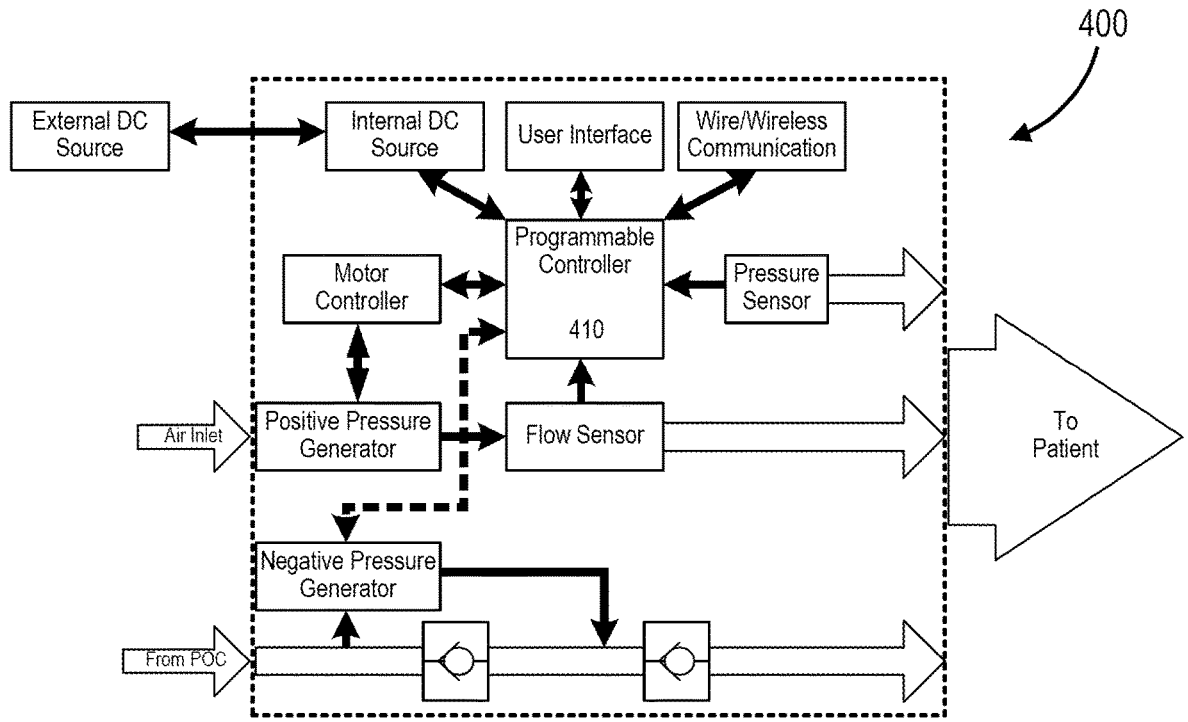
FIG. 7 is a system block diagram of one embodiment of the medical ventilator.

With reference to FIG. 7, an embodiment of a control unit 400 may take any well-known form in the art and includes a central microprocessor or CPU 410 in communication with the components of the system described herein via one or more interfaces, controllers, or other electrical circuit elements for controlling and managing the system. The system may include a user interface as part of the control unit or coupled to the control unit for allowing the user, provider, doctor, etc. to enter information, e.g., number of oxygen pulses, inspiratory positive air pressure, expiratory positive air pressure, flow rate, activity level, etc., to control the system.

Figure 8:
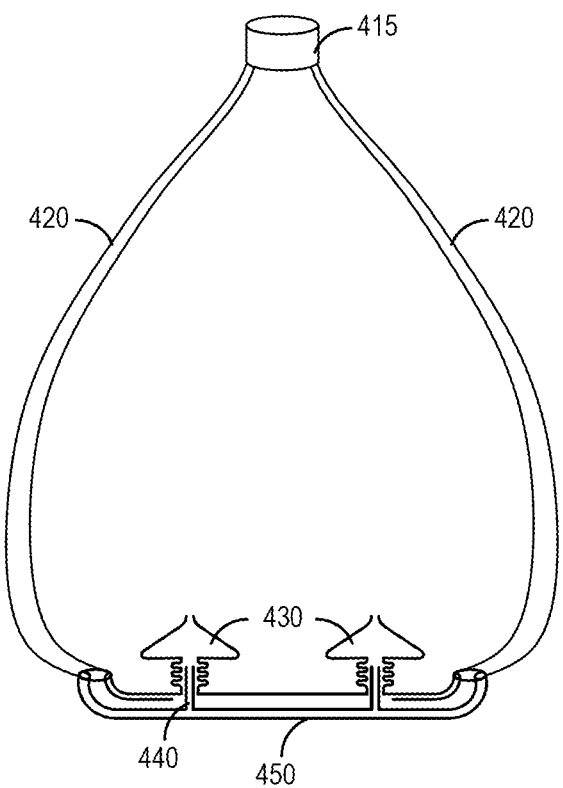
FIG. 8 is an embodiment of a pillows nasal interface with feeding tube.

With reference to FIG. 8, an embodiment of a pillows nasal interface 450 worn by a patient will be described. The interface 450 contains an oxygen cannula 440 integrated into the interface to deliver a pulse and/or pulses of oxygen to the patient to increase FIO2. Feeding tubes 420 contains a connector 415 to connect the interface to the patient/breathing circuit 250. The feed tubing 420 may be a thin flexible tube made of an inert material such as polyurethane, silicone, or another material known in the art. It will be noted that all components of the interface may be made of medical grade biocompatible materials. The medical ventilator 210 forces a gas such as air and/or oxygen through the tubing 420. The medical ventilator 210 may provide volume and/or pressure type of therapy delivered through the interface to the patient.

Figure 9A:
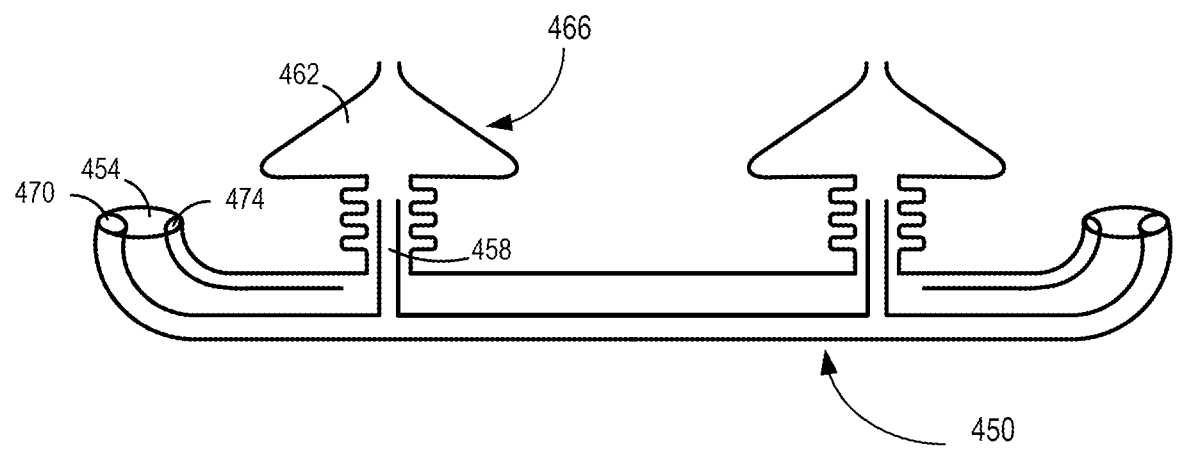
FIG. 9A is a cross sectional view of an embodiment of a pillows nasal interface with integrated nasal cannula.
Figure 9B:
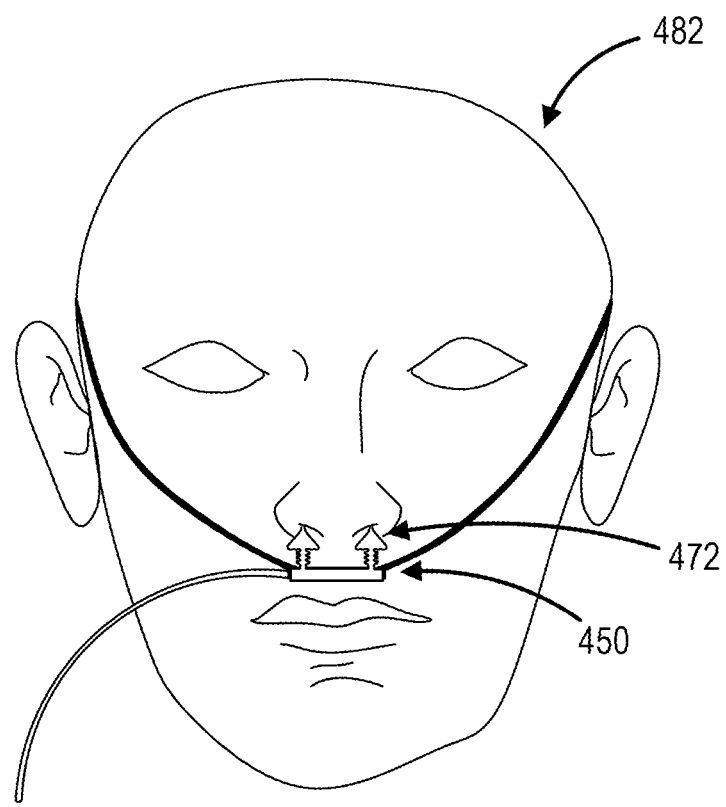
FIG. 9B is a front elevational view of the pillows nasal interface with integrated nasal cannula of FIG. 9B shown applied to the nostrils of a patient.

With reference to FIGS. 9A and 9B, an embodiment of the pillows interface 450 will be described in greater detail. Pressurized air from air delivery lumen 454 (from the ventilator 330) and oxygen gas from oxygen cannula/oxygen deliver lumens 458, 470 are mixed in a mixing chamber 462 of pillows 466. Lumen 474 is a triggering lumen. In an alternative embodiment, the oxygen cannula/oxygen deliver lumen 458 may be an opening in the tube and not extend all the way into the chamber 462 of the pillows 466. The pillows 466 seal at nostrils 478 of patient 482 and deliver the mixed gases from the chamber 462 of the pillows 466 to the patient 482.

System Overview

Infrastructure

Figure 10:
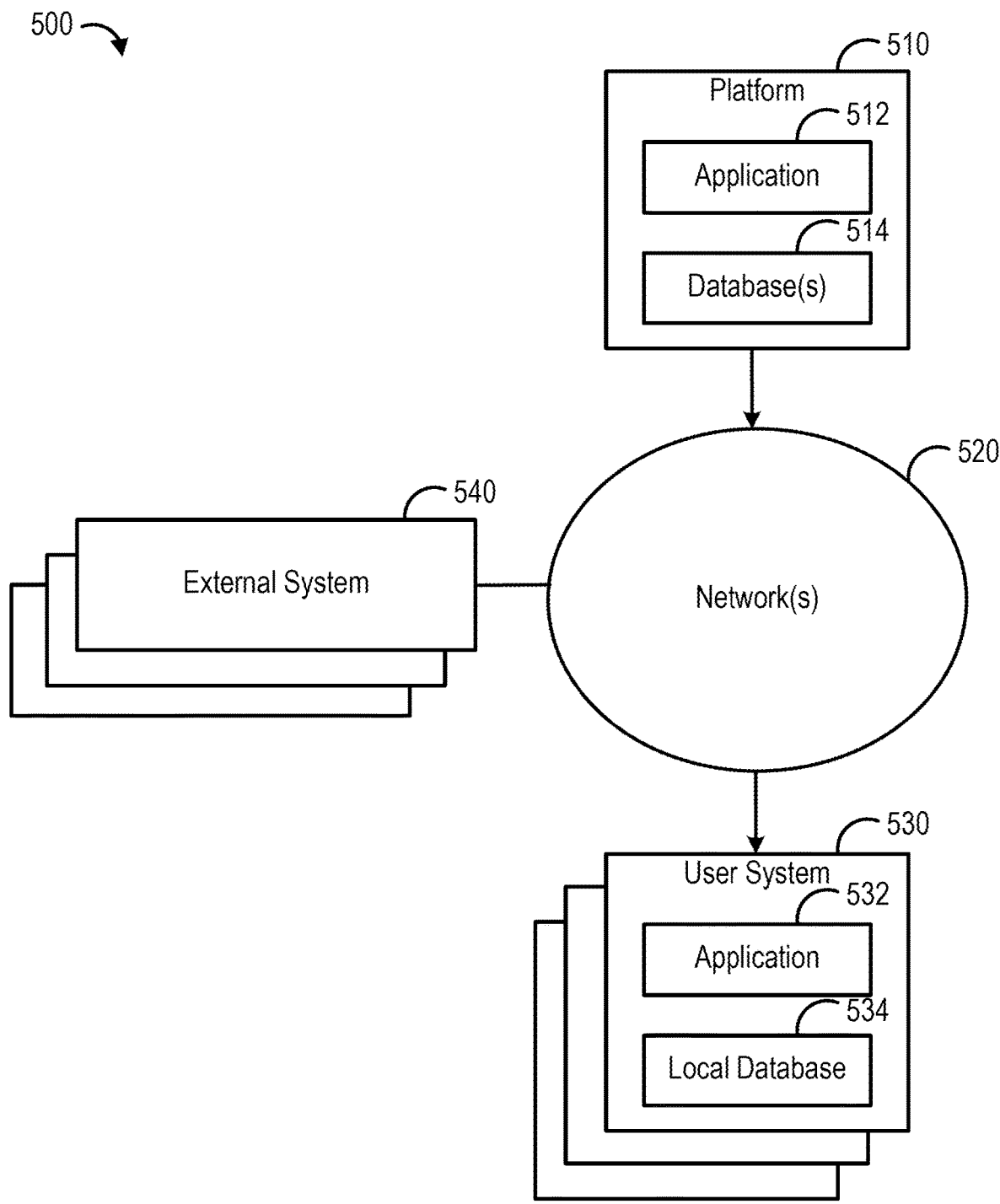
FIG. 10 illustrates an example infrastructure, in which one or more of the processes described herein, may be implemented, according to an embodiment.

FIG. 10 illustrates an example system 500 that may be used, for example, but not by way of limitation, for control and/or communication of/with the control unit 400 of the ventilator 210, according to an embodiment. The infrastructure may comprise a platform 510 (e.g., one or more servers) which hosts and/or executes one or more of the various functions, processes, methods, and/or software modules described herein. Platform 510 may comprise dedicated servers, or may instead comprise cloud instances, which utilize shared resources of one or more servers. These servers or cloud instances may be collocated and/or geographically distributed. Platform 510 may also comprise or be communicatively connected to a server application 512 and/or one or more databases 514. In addition, platform 510 may be communicatively connected to one or more user systems 530 via one or more networks 520. Platform 510 may also be communicatively connected to one or more external systems 540 (e.g., other platforms, websites, etc.) via one or more networks 520.

Network(s) 520 may comprise the Internet, and platform 510 may communicate with user system(s) 530 through the Internet using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 510 is illustrated as being connected to various systems through a single set of network(s) 520, it should be understood that platform 510 may be connected to the various systems via different sets of one or more networks. For example, platform 510 may be connected to a subset of user systems 530 and/or external systems 540 via the Internet, but may be connected to one or more other user systems 530 and/or external systems 540 via an intranet. Furthermore, while only a few user systems 130 and external systems 540, one server application 512, and one set of database(s) 514 are illustrated, it should be understood that the infrastructure may comprise any number of user systems, external systems, server applications, and databases.

User system(s) 530 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, Automated Teller Machines, and/or the like.

Platform 510 may comprise web servers which host one or more websites and/or web services. In embodiments in which a website is provided, the website may comprise a graphical user interface, including, for example, one or more screens (e.g., webpages) generated in HyperText Markup Language (HTML) or other language. Platform 510 transmits or serves one or more screens of the graphical user interface in response to requests from user system(s) 530. In some embodiments, these screens may be served in the form of a wizard, in which case two or more screens may be served in a sequential manner, and one or more of the sequential screens may depend on an interaction of the user or user system 530 with one or more preceding screens. The requests to platform 510 and the responses from platform 510, including the screens of the graphical user interface, may both be communicated through network(s) 520, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 514) that are locally and/or remotely accessible to platform 510. Platform 510 may also respond to other requests from user system(s) 530.

Platform 510 may further comprise, be communicatively coupled with, or otherwise have access to one or more database(s) 514. For example, platform 510 may comprise one or more database servers which manage one or more databases 514. A user system 530 or server application 512 executing on platform 510 may submit data (e.g., user data, form data, etc.) to be stored in database(s) 514, and/or request access to data stored in database(s) 514. Any suitable database may be utilized, including without limitation MySQL™, Oracle™, IBM™, Microsoft SQL™, Access™, and the like, including cloud-based databases and proprietary databases. Data may be sent to platform 510, for instance, using the well-known POST request supported by HTTP, via FTP, and/or the like. This data, as well as other requests, may be handled, for example, by server-side web technology, such as a servlet or other software module (e.g., comprised in server application 512), executed by platform 510.

In embodiments in which a web service is provided, platform 510 may receive requests from external system(s) 540, and provide responses in eXtensible Markup Language (XML), JavaScript Object Notation (JSON), and/or any other suitable or desired format. In such embodiments, platform 510 may provide an application programming interface (API) which defines the manner in which user system(s) 530 and/or external system(s) 540 may interact with the web service. Thus, user system(s) 530 and/or external system(s) 540 (which may themselves be servers), can define their own user interfaces, and rely on the web service to implement or otherwise provide the backend processes, methods, functionality, storage, and/or the like, described herein. For example, in such an embodiment, a client application 532 executing on one or more user system(s) 530 may interact with a server application 512 executing on platform 510 to execute one or more or a portion of one or more of the various functions, processes, methods, and/or software modules described herein. Client application 532 may be "thin," in which case processing is primarily carried out server-side by server application 512 on platform 510. A basic example of a thin client application is a browser application, which simply requests, receives, and renders webpages at user system(s) 530, while the server application on platform 510 is responsible for generating the webpages and managing database functions. Alternatively, the client application may be "thick," in which case processing is primarily carried out client-side by user system(s) 530. It should be understood that client application 532 may perform an amount of processing, relative to server application 512 on platform 510, at any point along this spectrum between "thin" and "thick," depending on the design goals of the particular implementation. In any case, the application described herein, which may wholly reside on either platform 510 (e.g., in which case server application 512 performs all processing) or user system(s) 530 (e.g., in which case client application 532 performs all processing) or be distributed between platform 510 and user system(s) 530 (e.g., in which case server application 512 and client application 532 both perform processing), can comprise one or more executable software modules that implement one or more of the functions, processes, or methods of the application described herein.

Example Processing Device

Figure 11:
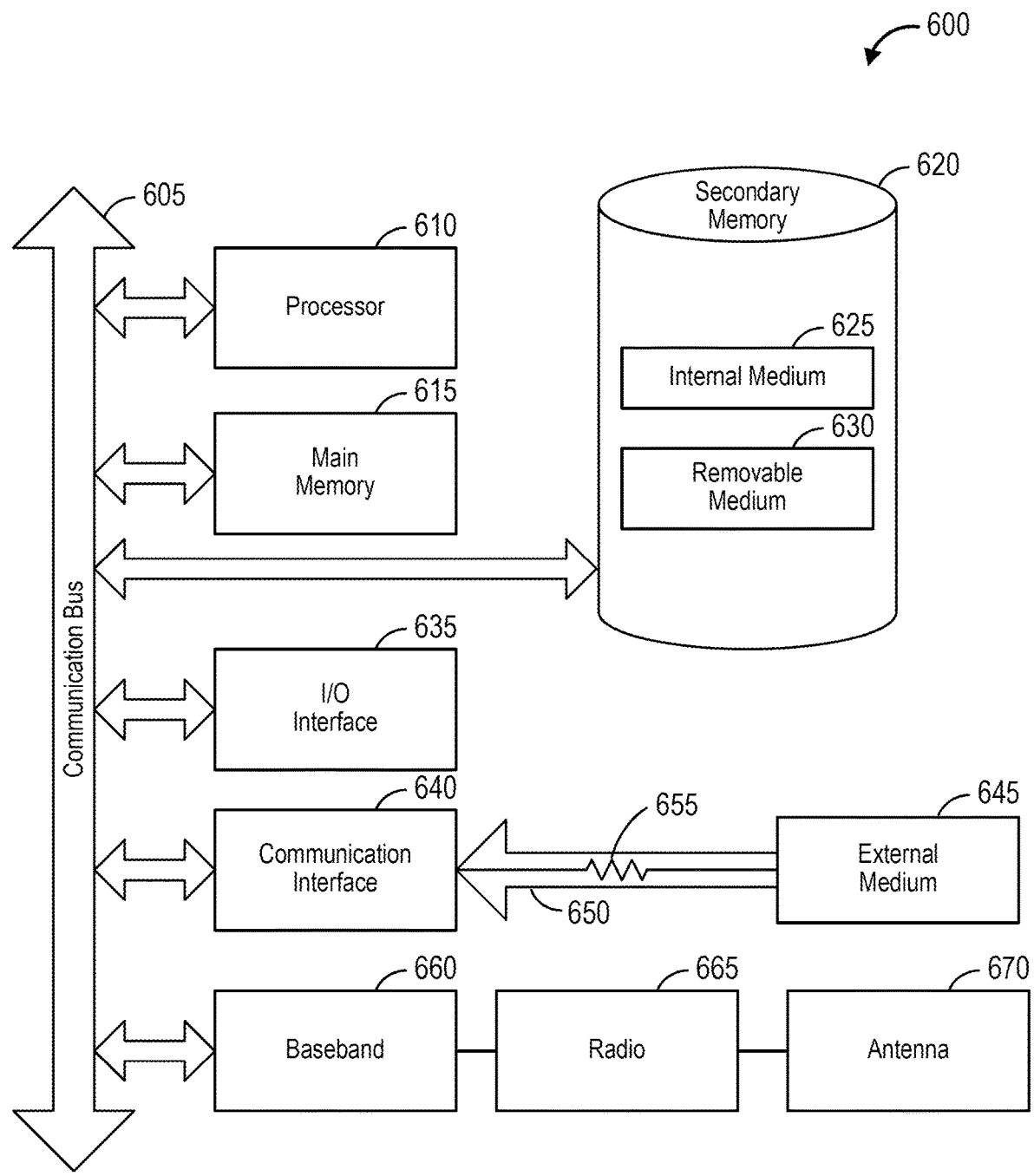
FIG. 11 illustrates an example processing system, by which one or more of the processed described herein, may be executed, according to an embodiment.

FIG. 11 is a block diagram illustrating an example wired or wireless system 600 that may be used in connection with various embodiments described herein such as, but not by way of limitation, the control unit 400 of the ventilator 210. For example, system 600 may be used as or in conjunction with one or more of the functions, processes, or methods (e.g., to store and/or execute the application or one or more software modules of the application) described herein, and may represent components of platform 510, user system(s) 530, external system(s) 540, and/or other processing devices described herein. System 600 can be a server or any conventional personal computer, or any other processor-enabled device that is capable of wired or wireless data communication. Other computer systems and/or architectures may be also used, as will be clear to those skilled in the art.

System 600 preferably includes one or more processors, such as processor 610. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 610. Examples of processors which may be used with system 600 include, without limitation, the Pentium® processor, Core i7® processor, and Xeon® processor, all of which are available from Intel Corporation of Santa Clara, California.

Processor 610 is preferably connected to a communication bus 605. Communication bus 605 may include a data channel for facilitating information transfer between storage and other peripheral components of system 600. Furthermore, communication bus 605 may provide a set of signals used for communication with processor 610, including a data bus, address bus, and/or control bus (not shown). Communication bus 605 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 600 preferably includes a main memory 615 and may also include a secondary memory 620. Main memory 615 provides storage of instructions and data for programs executing on processor 610, such as one or more of the functions and/or modules discussed herein. It should be understood that programs stored in the memory and executed by processor 610 may be written and/or compiled according to any suitable language, including without limitation C/C++, Java, JavaScript, Perl, Visual Basic, .NET, and the like. Main memory 615 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 620 may optionally include an internal medium 625 and/or a removable medium 630. Removable medium 630 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 620 is a non-transitory computer-readable medium having computer-executable code (e.g., disclosed software modules) and/or other data stored thereon. The computer software or data stored on secondary memory 620 is read into main memory 615 for execution by processor 610.

In alternative embodiments, secondary memory 620 may include other similar means for allowing computer programs or other data or instructions to be loaded into system 600. Such means may include, for example, a communication interface 640, which allows software and data to be transferred from external storage medium 645 to system 600. Examples of external storage medium 645 may include an external hard disk drive, an external optical drive, an external magneto-optical drive, and/or the like. Other examples of secondary memory 620 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 600 may include a communication interface 640. Communication interface 640 allows software and data to be transferred between system 600 and external devices (e.g. printers), networks, or other information sources. For example, computer software or executable code may be transferred to system 600 from a network server (e.g., platform 510) via communication interface 640. Examples of communication interface 640 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 600 with a network (e.g., network(s) 520) or another computing device. Communication interface 640 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 640 are generally in the form of electrical communication signals 655. These signals 655 may be provided to communication interface 640 via a communication channel 650. In an embodiment, communication channel 650 may be a wired or wireless network (e.g., network(s) 520), or any variety of other communication links. Communication channel 650 carries signals 655 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 615 and/or secondary memory 620. Computer programs can also be received via communication interface 640 and stored in main memory 615 and/or secondary memory 620. Such computer programs, when executed, enable system 600 to perform the various functions of the disclosed embodiments as described elsewhere herein.

In this description, the term "computer-readable medium" is used to refer to any non-transitory computer-readable storage media used to provide computer-executable code and/or other data to or within system 600. Examples of such media include main memory 615, secondary memory 620 (including internal memory 625, removable medium 630, and external storage medium 645), and any peripheral device communicatively coupled with communication interface 640 (including a network information server or other network device). These non-transitory computer-readable media are means for providing executable code, programming instructions, software, and/or other data to system 600.

In an embodiment that is implemented using software, the software may be stored on a computer-readable medium and loaded into system 600 by way of removable medium 630, I/O interface 635, or communication interface 640. In such an embodiment, the software is loaded into system 600 in the form of electrical communication signals 655. The software, when executed by processor 610, preferably causes processor 610 to perform one or more of the processes and functions described elsewhere herein.

In an embodiment, I/O interface 635 provides an interface between one or more components of system 600 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 600 may also include one or more optional wireless communication components that facilitate wireless communication over a voice network and/or a data network (e.g., in the case of user system 530). The wireless communication components comprise an antenna system 670, a radio system 665, and a baseband system 660. In system 600, radio frequency (RF) signals are transmitted and received over the air by antenna system 670 under the management of radio system 665.

In an embodiment, antenna system 670 may comprise one or more antennae and one or more multiplexors (not shown) that perform a switching function to provide antenna system 670 with transmit and receive signal paths. In the receive path, received RF signals can be coupled from a multiplexor to a low noise amplifier (not shown) that amplifies the received RF signal and sends the amplified signal to radio system 665.

In an alternative embodiment, radio system 665 may comprise one or more radios that are configured to communicate over various frequencies. In an embodiment, radio system 665 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 665 to baseband system 660.

If the received signal contains audio information, then baseband system 660 decodes the signal and converts it to an analog signal. Then the signal is amplified and sent to a speaker. Baseband system 660 also receives analog audio signals from a microphone. These analog audio signals are converted to digital signals and encoded by baseband system 660. Baseband system 660 also encodes the digital signals for transmission and generates a baseband transmit audio signal that is routed to the modulator portion of radio system 665. The modulator mixes the baseband transmit audio signal with an RF carrier signal, generating an RF transmit signal that is routed to antenna system 670 and may pass through a power amplifier (not shown). The power amplifier amplifies the RF transmit signal and routes it to antenna system 670, where the signal is switched to the antenna port for transmission.

Baseband system 660 is also communicatively coupled with processor 610, which may be a central processing unit (CPU). Processor 210 has access to data storage areas 615 and 620. Processor 610 is preferably configured to execute instructions (i.e., computer programs, such as the disclosed application, or software modules) that can be stored in main memory 615 or secondary memory 620. Computer programs can also be received from baseband processor 660 and stored in main memory 610 or in secondary memory 620, or executed upon receipt. Such computer programs, when executed, enable system 600 to perform the various functions of the disclosed embodiments.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A medical ventilator for delivering a pressurized breath to a patient and to use an oxygen source to increase FiO2 delivered to the patient, comprising:
    a positive pressure source; and
    a negative pressure source;
    wherein the negative pressure source is configured to trigger delivery of oxygen or a second gas.

2. The medical ventilator of claim 1, wherein the oxygen source delivers a continuous flow rate of oxygen.

3. The medical ventilator of claim 1, wherein the oxygen source is a pulsed oxygen concentrator that delivers pulses of a bolus of oxygen.

4. The medical ventilator of claim 3, wherein the negative pressure source is configured to trigger the oxygen source by generating a negative pressure in the ventilator at any time during patient inspiration and exhalation.

5. The medical ventilator of claim 3, wherein the ventilator is configured so that the negative pressure source causes multiple triggering of the oxygen source for oxygen bolus delivery during inspiration.

6. The medical ventilator of claim 1, wherein the ventilation delivery interface is a member selected from the group consisting of one or more intubation tubes, a non-rebreather mask, a partial rebreather mask, a full face mask, a total face mask, a nasal cannula, a nasal mask and a nasal pillow.

7. The medical ventilator of claim 1, wherein the ventilation delivery interface further includes a third lumen, which is at least one of triggering lumen and a monitoring lumen.

8. A method for delivering a pressurized breath to a patient and to trigger an oxygen source to increase FiO2 delivered to the patient with the medical ventilator of claim 1, comprising:
    triggering delivery of the first medical gas and the second medical gas with the third lumen;
    mixing the first medical gas and the second medical gas in the one or more mixing chambers of the ventilation delivery interface just prior to delivery to the patient and bypassing any interface leaks without mixing previously in the ventilator nor the ventilator circuit.

9. A medical ventilator for use with a supplemental oxygen source, the medical ventilator comprising:
   a positive pressure source configured to direct a positive pressure of an inhalation gas to a patient circuit for delivery to a patient; and
   a negative pressure source configured to generate and transmit a negative pressure to the supplemental oxygen source to trigger the supplemental oxygen source to direct oxygen to the patient circuit, via the medical ventilator, for delivery to the patient.

10. The medical ventilator of claim 9 wherein the negative pressure source is an electromechanical negative pressure device.

11. The medical ventilator of claim 9 wherein the positive pressure source is a blower.

12. The medical ventilator of claim 9, further comprising a controller configured to provide a signal to the negative pressure source to cause the negative pressure source to generate the negative pressure.

13. The medical ventilator of claim 9, further comprising a ventilator oxygen inlet configured to receive the oxygen from the supplemental oxygen source.

14. The medical ventilator of claim 9 wherein the negative pressure generated by the negative pressure source triggers delivery of a bolus of oxygen.

15. A medical ventilator system, comprising:
   a ventilator having (a) a positive pressure source configured to generate a positive pressure of an inhalation gas, and (b) a negative pressure source configured to generate and transmit a negative pressure to an oxygen source to trigger the oxygen source to release oxygen into the ventilator; and
   a patient circuit having a first lumen and a second lumen, wherein the patient circuit is configured to be coupled to the ventilator;
   wherein the system is further configured such that the positive pressure of inspiration gas is routed through the first lumen of the patient circuit and the oxygen is routed through the second lumen of the patient circuit.

16. The medical ventilator system of claim 15 wherein the ventilator further includes an inhalation gas outlet and an oxygen outlet, and wherein the first lumen is configured to be coupled to the inhalation gas outlet and the second lumen is configured to be coupled to the oxygen outlet.

17. The medical ventilator system of claim 15 wherein the ventilator further includes a ventilator oxygen inlet configured to receive the oxygen from the oxygen source before the oxygen is routed through the second lumen.

18. The medical ventilator system of claim 15 wherein the negative pressure source is an electromechanical negative pressure device.

19. The medical ventilator system of claim 15 wherein the positive pressure source is a blower.

20. The medical ventilator system of claim 15, further comprising a controller configured to provide a signal to the negative pressure source to cause the negative pressure source to generate the negative pressure.

* * * * *